US007695901B2

(12) United States Patent
Moyer et al.

(10) Patent No.: US 7,695,901 B2
(45) Date of Patent: Apr. 13, 2010

(54) IDENTIFICATION OF POINSETTIA CULTIVARS

(75) Inventors: James W. Moyer, Cary, NC (US); Elizabeth Parks, Stoney Creek, NC (US)

(73) Assignee: North Carolina State University, Raleigh, NC (US)

( * ) Notice: Subject to any disclaimer, the term of this patent is extended or adjusted under 35 U.S.C. 154(b) by 87 days.

(21) Appl. No.: 09/912,072

(22) Filed: Jul. 24, 2001

(65) Prior Publication Data

US 2003/0028916 A1    Feb. 6, 2003

Related U.S. Application Data

(60) Provisional application No. 60/220,854, filed on Jul. 26, 2000, provisional application No. 60/252,206, filed on Nov. 21, 2000.

(51) Int. Cl.
*C12Q 1/68* (2006.01)
*C12P 19/34* (2006.01)

(52) U.S. Cl. ........................ 435/6; 435/91.1; 435/91.2

(58) Field of Classification Search .................... 435/6, 435/91.1, 91.2; 536/22.2, 23.1
See application file for complete search history.

(56) References Cited

U.S. PATENT DOCUMENTS

| | | | | |
|---|---|---|---|---|
| 5,126,239 | A | 6/1992 | Livak et al. | 435/6 |
| 5,385,835 | A | 1/1995 | Helentjaris et al. | 172/172.3 |
| 5,413,909 | A | 5/1995 | Bassam et al. | 435/6 |
| 5,491,081 | A | 2/1996 | Webb | 435/172.3 |
| 5,871,697 | A | 2/1999 | Rothberg et al. | 422/68.1 |
| 5,874,215 | A | 2/1999 | Kuiper et al. | 435/6 |
| 5,955,276 | A | 9/1999 | Morgante et al. | 435/6 |
| 5,962,221 | A | 10/1999 | Caetano-Anolles | 435/6 |

OTHER PUBLICATIONS

Barker et al. Characterisation of Genetic Diversity in Potential Biomasss Willows (Salix spp.) by RAPD and AFLP analyses. Genome, (1999), v. 42, pp. 173-183.*
Dice, Lee R. Measures of the Amount of Ecologic Association Between Species. Ecology, (1945), v. 26, n.3, pp. 297-302.*
Ling et al. Identification of Poinsettia Cultivars Using RAPD Markers. HortScience, (1997), v. 321, n. 1, pp. 122-124.*
Sukhwinder et al. Genetic Diversity Analysis of Oryza Using Amplified Fragment Length Polymorphism. Crop Improv., (1998), v.25, n. 1, pp. 15-20.*
Tulloss, Rodham E. Assessment of Similarity Indices for Undesirable Properites and a New Tripartite Similarity Index Based o Cost Functions. Offprint from Palm M.E. and I.H. Chapela eds. (1997), Mycology in Sustainable Development: Expanding Concepts, Vanishing Borders., pp. 122-143.*
Loh et al. "Amplified fragment length polymorphisms (AFLP) provides molecular markers for the identification of C. bicolor Cultivars", Annals of Botany, vol. 84, pp. 155-161 (1999).*

Keim et al. "Molecular Diversity in *Bacillus anthracis*", J. Applied Microbiology, 1999, 87: 215-217.*
Anrold et al. "Predictive Fluorescent Amplified-fragment Length Polymorphism Analysis of *E. coli*: High Resolution Typing Method with Phyogenetic Significance", J Clin Microbiol. 199, 37: 1274-1279.*
Instruction Manual. "AFLP® Analysis System I AFLP Starter Primer Kit," *Life Technologies*.
Cerny et al. "Molecular Phylogney and DNA Amplification Fingerprinting of *Petunia* Taxa," *Theor Appl Genet* (1996) 92:1002-1016.
Dice, Lee R. "Measures of the Amount of Ecologic Association Between Species," *Ecology*, vol. 26, No. 3 (Jul. 1945), pp. 297-302.
Han et al. "Optimization of AFLP Fingerprinting of Organisms with a Large-Sized Genome: A Study on *Alstroemeria* spp," *Theor Appl Genet.* (1999) 98: pp. 465-471.
Ling et al. "Identification of Poinsettia Cultivars Using RAPD Markers," *HortScience* (1997) vol. 32, No. 1, pp. 122-124.
Lynch, Michael. "Estimation of Relatedness by DNA Fingerprinting," *Mol. Biol. Evol.* (1988) vol. 5, No. 5, pp. 584-599.
Starman et al. Abstract. "Distinguishing Poinsettia Cultivars and Evaluating Their Genetic Relationships using DNA Fingerprinting," *HortScience.* (Jun. 1997) vol. 32, Issue 3.
Starman et al. "Nucleic Acid Scanning Techniques Distinguishing Closely Related Cultivars of Poinsettia," *HortScience.* (1999) vol. 34, Issue 6, pp. 1199-1122.
Vos et al. "AFLP: a new technique for DNA fingerprinting," *Nucleic Acids Research.* (1995) vol. 23, No. 21, pp. 4407-4414.
Wolff et al. "Identification of chrysanthemum cultivars and stability of DNA fingerprint patterns," *Theor Appl Genet* (1995) vol. 91, pp. 439-447.
Barcaccia, et al., "AFLP fingerprinting in *pelargonium peltatum*: its development and potential in cultivar identification," *Journal of Horticulture Science and Biotechnology* 74: 2 243-250 (1999).
Han, et al, "Genetic Diversity of Chilean and brazilian *alstroemeria* species assessed by AFLP analysis," *Heredity* 84: 564-569 (2000).
Han, et al, "Optimization of AFLP fingerprinting of organisms with a large-sized genome: a study of *alstroemeria* spp.," *Theor. Appl. Genet.* 98: 465-471 (1999).
Hill, et al, "PCR-based fingerprinting using AFLPs as a tool for studying genetic relationships in *lactuca* spp.," *Theor. Appl. Genet.* 93: 1202-1210 (1996).
Mace, et al, "AFLP analysis of genetic relationships among the cultivated eggplant, solanum melongena l., and wild relatives (solanaceae)," *Theor. Appl. Genet.* 99: 626-633 (1999).
Zhang, et al., "Differentiation of bermudagrass (*cynodon* spp.) genotypes by AFLP analyses," *Theor. Appl. Genet.* 98: 895-902 (1999).

* cited by examiner

*Primary Examiner*—Sarae Bausch
(74) *Attorney, Agent, or Firm*—Myers Bigel Sibley & Sajovec, P.A.

(57) ABSTRACT

Methods of determining whether a plant is a member of a known cultivar utilize DNA fingerprinting techniques and the discovery of 41 polymorphic fragments that correlate with cultivar identity. These methods are useful in determining whether a plant is a member of a particular breeding family and potentially whether plants are genetically similar to each other.

16 Claims, 3 Drawing Sheets

SEQUENCE LISTING

<160> NUMBER OF SEQ ID NOS: 54

<210> SEQ ID NO 1
<211> LENGTH: 372
<212> TYPE: DNA
<213> ORGANISM: Euphorbia pulcherrima
<220> FEATURE:
<221> NAME/KEY: misc_feature
<222> LOCATION: (24)..(24)
<223> OTHER INFORMATION: "n" represents any nucleotide.

```
<221> NAME/KEY: misc_feature
<222> LOCATION: (195)..(195)
<223> OTHER INFORMATION: "n" represents any nucleotide.

<400> SEQUENCE: 1
aaacttagac tttataccat aatnttttag ttgctgcttg atctatagca gttgagccac      60
ataacttctg gcagccatgt actcagcttc agctgtactt agagccatag aagtttattt     120
cttgttgtac catgtgtcta gacaattacc aaggaaatga catcctctag tggtgttttt     180
cctttctaac ttgtntcttc cataattagc atttgtgtat gccctcagag tgaaatttcc     240
atttcttgga taccataaac ctgcatcaat agttcctagc aaataccata acaacagcta     300
agtgagattc tctggggtta gcttgatatc taccataata acatacaaca tattgaattt     360
caggcctact ag                                                         372

<210> SEQ ID NO 2
<211> LENGTH: 198
<212> TYPE: DNA
<213> ORGANISM: Euphorbia pulcherrima
<220> FEATURE:
<221> NAME/KEY: misc_feature
<222> LOCATION: (35)..(35)
<223> OTHER INFORMATION: "n" represents any nucleotide.
<221> NAME/KEY: misc_feature
<222> LOCATION: (45)..(45)
<223> OTHER INFORMATION: "n" represents any nucleotide.
<221> NAME/KEY: misc_feature
<222> LOCATION: (48)..(48)
<223> OTHER INFORMATION: "n" represents any nucleotide.
<221> NAME/KEY: misc_feature
<222> LOCATION: (154)..(154)
<223> OTHER INFORMATION: "n" represents any nucleotide.
<221> NAME/KEY: misc_feature
<222> LOCATION: (160)..(160)
<223> OTHER INFORMATION: "n" represents any nucleotide.

<400> SEQUENCE: 2
gttagaaaag caaatttcag tgcagggtgt ggatntggtg ccagntanta ttgcaaatgt      60
tagagctttg ttgcaggatt tgactgagag gaattgtgtc atggagagaa gttcgagtgc     120
gagcccgatt gtgttgtagg agaagaaatt gganagaagn cgttggggc aagtatggag      180 ttgagaatcc cacatcta                                                   198

<210> SEQ ID NO 3
<211> LENGTH: 182
<212> TYPE: DNA
<213> ORGANISM: Euphorbia pulcherrima

<400> SEQUENCE: 3
agttagaaaa gcaaatttca gtgcagggta tactattgca aatgttagag ctttgttgca      60
ggatttgaca gagggaatt gtatcatgga gagaagttcg agtgcgagcc cgattgtgtt     120
gtaggagaag aaattggaag aagacgttgg gggcaagtgt ggagttgaga atcccacatg     180
ta                                                                    182

<210> SEQ ID NO 4
<211> LENGTH: 161
<212> TYPE: DNA
<213> ORGANISM: Euphorbia pulcherrima

<400> SEQUENCE: 4
tgcttccaag gtgtttctcc ttttgataga gaaattttac caactatgga aaactgacat      60
gatttcagcc tctcttcata aagattttga ggaatctgaa ttgctttgta tctcccactt     120
```

```
gcgtcaatga tttgtgagtt cagggttgga gcagatatct a                    161
```

<210> SEQ ID NO 5
<211> LENGTH: 103
<212> TYPE: DNA
<213> ORGANISM: Euphorbia pulcherrima

<400> SEQUENCE: 5

```
cgacgatggc aatgatgaca attcttgcct ggaaccagaa atgataattg atactcccta   60
tatagggaga atgttgaaaa ttagattttg aagttgttat tta                    103
```

<210> SEQ ID NO 6
<211> LENGTH: 371
<212> TYPE: DNA
<213> ORGANISM: Euphorbia pulcherrima
<220> FEATURE:
<221> NAME/KEY: misc_feature
<222> LOCATION: (81)..(81)
<223> OTHER INFORMATION: "n" represents any nucleotide.

<400> SEQUENCE: 6

```
ttccatggta cctttgttca gtaaaaaaat tacacaatta gctagttcga agaatacacg   60
tgcaaactaa ttttaggtc ntggttgcaa attattttgc aaaaataatt accaagctat   120
ctcttccaag tatatattc tctagcatct cccatgcata agaactgttg gagtgtatat   180
gtatgagaaa gaaatgtata ataccaacct cttccatttg ctttgttcta ctgctttcca   240
agtgctcggt ttaggtgtat tacaaggccc tatagtagcc tgcagtcatt catggaacta   300
acaaactcag tatctaagcc cggggtgaaa agatactcac aatctcacat ttccgatcaa   360
ctccccatat c                                                       371
```

<210> SEQ ID NO 7
<211> LENGTH: 247
<212> TYPE: DNA
<213> ORGANISM: Euphorbia pulcherrima
<220> FEATURE:
<221> NAME/KEY: misc_feature
<222> LOCATION: (22)..(22)
<223> OTHER INFORMATION: "n" represents any nucleotide.
<221> NAME/KEY: misc_feature
<222> LOCATION: (151)..(151)
<223> OTHER INFORMATION: "n" represents any nucleotide.
<221> NAME/KEY: misc_feature
<222> LOCATION: (175)..(175)
<223> OTHER INFORMATION: "n" represents any nucleotide.

<400> SEQUENCE: 7

```
gaaaatatgt gctgaattta tnctgtaaag tagtttcgat gcaaccactg tttagcttat   60
acttaacttt ctgttcatca ccatcaatcc tcagcaaaac accctcattc ttcatactta  120
gatgttgttc aagaaatat ggggtaacag ngatttcttt gccctggacc ttggnttgaa  180
gagcatcaaa cttggcgtga acactaagaa tctcatagaa ctcccttgac taagtcagga  240
tatgtgg                                                            247
```

<210> SEQ ID NO 8
<211> LENGTH: 221
<212> TYPE: DNA
<213> ORGANISM: Euphorbia pulcherrima

<400> SEQUENCE: 8

```
agctcttcat tgcttcatca taggttatcg gtttatcatc ctctatgata tatagttccc   60
```

```
tacatcagtg atgatgcaac catatctttt aggaccgtta tgaatatgac ctgatctttg      120
cattgattgt gtttcaacag gttgttcatt ggatcaaacc ttcttgtgta tctagaatgg      180
ggtcaactag ttgattatct gttttatatt cttgaagctc c                         221
```

<210> SEQ ID NO 9
<211> LENGTH: 176
<212> TYPE: DNA
<213> ORGANISM: Euphorbia pulcherrima

<400> SEQUENCE: 9

```
tgcattccat ggttcaaaag ccgagtttct tcgcctcatc gagtttttat tcgcaaagtg       60
gatggtttag acagggtttt gaccagcagc ctggagttgg gagattgttg gcctcatcag      120
aaattagttt tcatggagtt gggagatttg aaggtaattc aaggaagttt tctgca          176
```

<210> SEQ ID NO 10
<211> LENGTH: 73
<212> TYPE: DNA
<213> ORGANISM: Euphorbia pulcherrima
<220> FEATURE:
<221> NAME/KEY: misc_feature
<222> LOCATION: (54)..(54)
<223> OTHER INFORMATION: "n" represents any nucleotide.

<400> SEQUENCE: 10

```
ccggataaaa gcactacaat caggtagatg actcgggtcg gatacgtagt gcantactga       60
gtcagactaa cga                                                          73
```

<210> SEQ ID NO 11
<211> LENGTH: 75
<212> TYPE: DNA
<213> ORGANISM: Euphorbia pulcherrima

<400> SEQUENCE: 11

```
gtttatcttc aagtctaaca agacccagtt tttcagattc ctttcctcaa tttctcgttc       60
agttataaaa gctaa                                                        75
```

<210> SEQ ID NO 12
<211> LENGTH: 64
<212> TYPE: DNA
<213> ORGANISM: Euphorbia pulcherrima
<220> FEATURE:
<221> NAME/KEY: misc_feature
<222> LOCATION: (52)..(52)
<223> OTHER INFORMATION: "n" represents any nucleotide.

<400> SEQUENCE: 12

```
gaatgcctat tacatcggaa aacaaaaaaa caaagataaa tgctagagac antataatca       60
tccc                                                                    64
```

<210> SEQ ID NO 13
<211> LENGTH: 59
<212> TYPE: DNA
<213> ORGANISM: Euphorbia pulcherrima

<400> SEQUENCE: 13

```
gtctttctag ttttactgat ttctgttgta cttctattag atatatattg tatatctga        59
```

<210> SEQ ID NO 14
<211> LENGTH: 49
<212> TYPE: DNA
<213> ORGANISM: Euphorbia pulcherrima

<400> SEQUENCE: 14
ttgaaggcag gaaaatatat cctattctga aaggatttac aatctgcgg                49

<210> SEQ ID NO 15
<211> LENGTH: 216
<212> TYPE: DNA
<213> ORGANISM: Euphorbia pulcherrima

<400> SEQUENCE: 15
acttctctcc ccacacaatg tgtagtgcag ctagtgccga tgacagtgag aagaccagaa    60
tcacatagag agcgatcgta tgaaaaggta ttgaattagg gatttgatga aagggtaaga   120
tagaaaggga gttggtgtta gcgagttgtt tctcctgccc tcacaataat acttttatca   180
atttttcagt aacaatttgt ccatgtactt ttggac                             216

<210> SEQ ID NO 16
<211> LENGTH: 120
<212> TYPE: DNA
<213> ORGANISM: Euphorbia pulcherrima

<400> SEQUENCE: 16
tgtgctcttg ttccttggat caaataagga aacatggcct taggtaagtg tagtcatatc    60
tttttggctc atgaaccata agtcccctat agtttgaaca aggttgtgta ggattggtat   120

<210> SEQ ID NO 17
<211> LENGTH: 120
<212> TYPE: DNA
<213> ORGANISM: Euphorbia pulcherrima

<400> SEQUENCE: 17
agaacctaat ctaagtagaa tcttataaaa gaaatgaaaa ctttgagaga tattttagt    60 atgaaaatag aaaataaatc ataaagtaaa caagcacaaa taccagctgg attttctaa   120

<210> SEQ ID NO 18
<211> LENGTH: 118
<212> TYPE: DNA
<213> ORGANISM: Euphorbia pulcherrima

<400> SEQUENCE: 18
gaatgtgctc ttggtccttg ggatctaaat aaggaaacat ggccttggta tagtaataat    60 acttttgct cataaccctg agtccgctat ggctgaacaa ggttgtgcag gatggtat      118

<210> SEQ ID NO 19
<211> LENGTH: 117
<212> TYPE: DNA
<213> ORGANISM: Euphorbia pulcherrima

<400> SEQUENCE: 19
agaacctaaa tctaggtagc cttcttataa aagaaaatga aactttgag agatattttt    60 agtatgaaaa tagaaaataa aatcataagt aacagcacaa ttaccagctg gactctc     117

<210> SEQ ID NO 20
<211> LENGTH: 109
<212> TYPE: DNA
<213> ORGANISM: Euphorbia pulcherrima

<400> SEQUENCE: 20
gaatgtgctc ttggttcctt agggatctaa ataaggaaac atggcttggt atagtaataa    60

| tactttttggc tcatgaactc tagtcctatg ctacaggtgt cagatgata | 109 |

<210> SEQ ID NO 21
<211> LENGTH: 114
<212> TYPE: DNA
<213> ORGANISM: Euphorbia pulcherrima

<400> SEQUENCE: 21

| gatgtgctct tggtcctgga tctaatgaaa catgccttgt attagtaaaa atacctttt | 60 |
| ggctatgaac cctgagtccc ctatggcttg aaaaaggttg tgcaggattg gtat | 114 |

<210> SEQ ID NO 22
<211> LENGTH: 119
<212> TYPE: DNA
<213> ORGANISM: Euphorbia pulcherrima

<400> SEQUENCE: 22

| tttctctctg attacattac tatgtaaaga cctaaatgaa tgagttttct tcgcaaggac | 60 |
| caaatcgaga tattttaact aattttttct cttgaaatat tttatctaga tgaaatttt | 119 |

<210> SEQ ID NO 23
<211> LENGTH: 116
<212> TYPE: DNA
<213> ORGANISM: Euphorbia pulcherrima

<400> SEQUENCE: 23

| gctttcttac attcttgggg acaagaatgc tttgaagggg agggtattgt caggaggaag | 60 |
| taatataatc tgattgttat ttagtttatt tgctttgggt aaataagttg actatg | 116 |

<210> SEQ ID NO 24
<211> LENGTH: 336
<212> TYPE: DNA
<213> ORGANISM: Euphorbia pulcherrima
<220> FEATURE:
<221> NAME/KEY: misc_feature
<222> LOCATION: (333)..(333)
<223> OTHER INFORMATION: "n" represents any nucleotide.

<400> SEQUENCE: 24

| ctccaaggct tcattgatgc agattatggt agagatactc ttgagagaaa gagtacatca | 60 |
| gaggttgtca cttctaggga gattgcttag tatcttggta cagcaagaag caaacttcag | 120 |
| ttgctttatc tactatagaa gtagaatata tggcagctag aagttgtgta gctcaacttc | 180 |
| tttggatcaa gcaacaacta gaagattatg gagtctaatc cgggtgtgtg gatgtaatgt | 240 |
| gtgattacaa aagtgccatt gatgtgtcaa acaatccagt attccatagg aggataaaac | 300 |
| atgtcaacat aaggcatcgt gaagagaaga anttg | 336 |

<210> SEQ ID NO 25
<211> LENGTH: 232
<212> TYPE: DNA
<213> ORGANISM: Euphorbia pulcherrima
<220> FEATURE:
<221> NAME/KEY: misc_feature
<222> LOCATION: (6)..(6)
<223> OTHER INFORMATION: "n" represents any nucleotide.
<221> NAME/KEY: misc_feature
<222> LOCATION: (26)..(26)
<223> OTHER INFORMATION: "n" represents any nucleotide.

<400> SEQUENCE: 25

| cagganatga actttgattt caccancata gattttgaat ctcagtcttc aggaagcttt | 60 |

```
ttcagttctt gagcacatgt tctgaaaaaa tatcaaatct ctacattgtt ttcaaggtca    120
acaaatgacc ggtaaggctc gggttggtct agaccgggca catcaatttg gggacaaatt    180
tgaatccatt ttatcctact tttttgtatt ggcagtaagg attaggattc tc            232
```

<210> SEQ ID NO 26
<211> LENGTH: 167
<212> TYPE: DNA
<213> ORGANISM: Euphorbia pulcherrima
<220> FEATURE:
<221> NAME/KEY: misc_feature
<222> LOCATION: (73)..(73)
<223> OTHER INFORMATION: "n" represents any nucleotide.

<400> SEQUENCE: 26

```
ctctcctata ttttagggtt tagctttgta tcataagctc ttctgctctc tacccctcta     60
aaccacccca tgntatatat ggtattcatc actcgaatat ttatgtaagt catccatctc    120
attcagggtt tgattcgggc tgatcatctt ccggtttctc tagctaa                  167
```

<210> SEQ ID NO 27
<211> LENGTH: 102
<212> TYPE: DNA
<213> ORGANISM: Euphorbia pulcherrima

<400> SEQUENCE: 27

```
tttgcaggag tactgtccat gtaaatttga gacttcgcac tatcattgca agcaatagca     60
atagaagaaa catcattttg cagcttacta atacacccac tc                       102
```

<210> SEQ ID NO 28
<211> LENGTH: 308
<212> TYPE: DNA
<213> ORGANISM: Euphorbia pulcherrima

<400> SEQUENCE: 28

```
gcctagaaag gttttctagt caacatactc acgtagctca cttttacccct aacttttgcc    60 tagaacgtcc tttttgaatt ttcagtctag cgggctattt tgcaccctaa cttttgcctg   120
aatggtttgt agaataccaa atagcgggat atgccctaat tttgcctaag cagtagagga   180
ccactcatcg ggtgatttat tttgattatt ttttgtgtgc cgcttttctg gatttgattc   240
ttttagatta gatatgataa tgcttcaatc gatcctgatt gatagggttt gtgaattggt   300
acgcagcc                                                            308
```

<210> SEQ ID NO 29
<211> LENGTH: 137
<212> TYPE: DNA
<213> ORGANISM: Euphorbia pulcherrima

<400> SEQUENCE: 29

```
aagaccaagt caggagcata cctaagaaga aggaatagct gacctagccg atcctctggt     60
acctcaacta tggatggacc cccgtgtacc tctcagtcct cctcctcgtc atcatatcat   120
catcctcgtt gttgctc                                                  137
```

<210> SEQ ID NO 30
<211> LENGTH: 135
<212> TYPE: DNA
<213> ORGANISM: Euphorbia pulcherrima

<400> SEQUENCE: 30

```
ttatcataat caatgtcaat aaaaaaaaaa aggcaataaa taaaagataa ataattctga     60
```

```
tagactaaaa agagcaaggc tgatgcaaaa gtcagaataa gtctgctgga ttgaaatcga    120
aaggtatcta ggcaa                                                    135

<210> SEQ ID NO 31
<211> LENGTH: 139
<212> TYPE: DNA
<213> ORGANISM: Euphorbia pulcherrima
<220> FEATURE:
<221> NAME/KEY: misc_feature
<222> LOCATION: (128)..(128)
<223> OTHER INFORMATION: "n" represents any nucleotide.

<400> SEQUENCE: 31 ggcccttct cagccatgat atctaaatat acgagtcttg tgtgtacgcc attgcatctc     60
tagcccttct ccaggggcg ttctcatctt gtccatgcca aatacaatt tcatatattc    120 tctctccnag taagcaacc                                                139

<210> SEQ ID NO 32
<211> LENGTH: 281
<212> TYPE: DNA
<213> ORGANISM: Euphorbia pulcherrima

<400> SEQUENCE: 32
aacctcatca atcaggatca gatgaagcat tatcatatct aatcgaaaag aatcaaatct    60
agaaaagcgg cacataaaag tatataaaaa aatcacccga cgagtagtct tctactgctc   120
aggcaaaaat tagggtgtat cctgttgttt ggtaatctgt aaaccattca ggaaaatgtt   180
agggtgcaag aataacccgc tagactgaaa atctgaaaag gatggtctag gcaaaattta   240
gggtaaaagt gagctacaat agtgtgttgg cttgaaaact t                      281

<210> SEQ ID NO 33
<211> LENGTH: 211
<212> TYPE: DNA
<213> ORGANISM: Euphorbia pulcherrima

<400> SEQUENCE: 33
ggattactga taatgttgac aatggcttga gggcagtatc ttgcaactcc ctcgcaaagg    60
gttttcacta ttccggcatt tatgttgaat aaatcgtccc tagtcattcc tggcttccta   120
ggaaccccag caggaattat cacaagatcc attcctgtaa gagcatcgtc tagttgctgc   180
tggcccaaga aaccacgcac ctgaaaatca t                                  211

<210> SEQ ID NO 34
<211> LENGTH: 320
<212> TYPE: DNA
<213> ORGANISM: Euphorbia pulcherrima
<220> FEATURE:
<221> NAME/KEY: misc_feature
<222> LOCATION: (127)..(127)
<223> OTHER INFORMATION: "n" represents any nucleotide.
<221> NAME/KEY: misc_feature
<222> LOCATION: (136)..(136)
<223> OTHER INFORMATION: "n" represents any nucleotide.
<221> NAME/KEY: misc_feature
<222> LOCATION: (142)..(142)
<223> OTHER INFORMATION: "n" represents any nucleotide.
<221> NAME/KEY: misc_feature
<222> LOCATION: (148)..(148)
<223> OTHER INFORMATION: "n" represents any nucleotide.
<221> NAME/KEY: misc_feature
<222> LOCATION: (192)..(192)
<223> OTHER INFORMATION: "n" represents any nucleotide.
<221> NAME/KEY: misc_feature
```

<222> LOCATION: (213)..(213)
<223> OTHER INFORMATION: "n" represents any nucleotide.

<400> SEQUENCE: 34

```
ttagctcgat ctccatgatc acaaaactag ttatcacacc caccatttac attgttgtta      60
tgcaacaaag tcaactgtac tagagattct cgtcccgaag tgccctcaag atgggatcgt     120
tttcttnatc tatgtngtag tngtcgtngt cgtcatcatc caggtcatcc agtattgatt     180
ggttgatcct tntgcgagac tttcttctat gcnttcttgg gctccaaacg aggttcagct     240
tgctgtactc ccatatcacc cactttgaac ctgcagagta gcataacgaa caagaaaatg     300
aatgatagta gaataaattt                                                 320
```

<210> SEQ ID NO 35
<211> LENGTH: 272
<212> TYPE: DNA
<213> ORGANISM: Euphorbia pulcherrima

<400> SEQUENCE: 35

```
tatggtattt cttttctggg tgtaattgat ttgcaacttg agtcaaacag gttctatcaa      60
ctgattttc tagttttcgg cgcttactgc aaccctggaa aggatgttca ctgttttttc     120
cttcgttttc caggtcagca atacgacgag taatttcctc ggtatcatat atggattcca     180
gcttgtaatc ttttatgcat tgaaatacgg ctttacgagc agctagttct ctctcccctgg    240
ccttctcctg cagatgaaat caggagttat at                                   272
```

<210> SEQ ID NO 36
<211> LENGTH: 195
<212> TYPE: DNA
<213> ORGANISM: Euphorbia pulcherrima

<400> SEQUENCE: 36

```
cagattattt gactataatt agtttggctt ctatggttgc tgcactaaat gatcatcgaa      60
acagccaatc ggttcatggg tttgtcatga gaaaaggctg ttcatggaa tatattgtca     120
ttgggaatgc aactgtggac atgtatgcta aaattggagc cacagatacg gcccgtgcag     180
tatttgaaag cctac                                                      195
```

<210> SEQ ID NO 37
<211> LENGTH: 171
<212> TYPE: DNA
<213> ORGANISM: Euphorbia pulcherrima

<400> SEQUENCE: 37

```
tttcaaaagt tgaaagaat atgtcataag ccttacacta gtaaatggaa ctatagtccg       60
tgcccctac atcaaaagat caatgataaa gaagaacaaa acactccaaa gagcaattct     120
tctcaaaagg tgctgagctg gaatcccatt ctaatcgtgg catccctccc c              171
```

<210> SEQ ID NO 38
<211> LENGTH: 120
<212> TYPE: DNA
<213> ORGANISM: Euphorbia pulcherrima

<400> SEQUENCE: 38

```
aaatgtagca aagaacatta tcaacaaatg ccccaaaaaa caagtgaaaa tataatcacc      60
actgaagcaa aaaagtaag taaaaacaga agaaaagaca actaaatgta gattattaca     120
```

<210> SEQ ID NO 39

```
<211> LENGTH: 88
<212> TYPE: DNA
<213> ORGANISM: Euphorbia pulcherrima

<400> SEQUENCE: 39 aactttttc tttgtataat tatctcatat tttttgtgaa tattcttgtt tgaatagaac      60
acactttata tatgaaaccc actttatc                                        88

<210> SEQ ID NO 40
<211> LENGTH: 67
<212> TYPE: DNA
<213> ORGANISM: Euphorbia pulcherrima

<400> SEQUENCE: 40 atcctttca caaggacat cgatgaaaag tgatttataa atgtggatat gtaaatctag       60
cttagtg                                                              67

<210> SEQ ID NO 41
<211> LENGTH: 223
<212> TYPE: DNA
<213> ORGANISM: Euphorbia pulcherrima

<400> SEQUENCE: 41
ccaggagtaa atagccatt atgaaagtac cattgaacca tattgctaac atccttgccg      60
accaggtccc aaaagtgttg ataaaaaata ccagtaaagc cgtcaggacc cagcgcacta   120
tcacccttca tcgagaagac tctatttcga atttcatcaa agaaggctt cctaatgaac    180 tcatcattgt cgctgcccgt cacccgatta ggaactgtct gcc                      223

<210> SEQ ID NO 42
<211> LENGTH: 165
<212> TYPE: DNA
<213> ORGANISM: Euphorbia pulcherrima

<400> SEQUENCE: 42
ctaactggat gcaagaaatg agcaggcacc gatgaactag caaataaagg tggcagcatc     60
agaaccacca tcgtaaccac cgttagaatc gccgcccgat gaaagcccct gcattctttt   120
caaatacaat ctatacttct tgcatcatga accctacgtt ttctc                   165

<210> SEQ ID NO 43
<211> LENGTH: 106
<212> TYPE: DNA
<213> ORGANISM: Euphorbia pulcherrima

<400> SEQUENCE: 43
actaatccca tattagatgg gaattggatc gcttgacatg agagatttca aatgaacttt     60
atttccatcc ctagagccga gttcataaaa tctctcctaa acccat                  106

<210> SEQ ID NO 44
<211> LENGTH: 67
<212> TYPE: DNA
<213> ORGANISM: Euphorbia pulcherrima
<220> FEATURE:
<221> NAME/KEY: misc_feature
<222> LOCATION: (51)..(51)
<223> OTHER INFORMATION: "n" represents any nucleotide.

<400> SEQUENCE: 44
tgcaccattt gcattttcac acaaccattt ataataatat tcatcccata ngtttgaggg     60
ttttcgg                                                              67
```

-continued

<210> SEQ ID NO 45
<211> LENGTH: 50
<212> TYPE: DNA
<213> ORGANISM: Euphorbia pulcherrima
<220> FEATURE:
<221> NAME/KEY: misc_feature
<222> LOCATION: (23)..(23)
<223> OTHER INFORMATION: "n" represents any nucleotide.
<221> NAME/KEY: misc_feature
<222> LOCATION: (47)..(47)
<223> OTHER INFORMATION: "n" represents any nucleotide.

<400> SEQUENCE: 45
gttcgtatat gtaatatatc ctngtaaagt ttaattacag aaacatngca            50

<210> SEQ ID NO 46
<211> LENGTH: 64
<212> TYPE: DNA
<213> ORGANISM: Euphorbia pulcherrima

<400> SEQUENCE: 46
cgtaccagcg agacgatgg cctgaaattt gagcaccttc cgttgcatca gagtttctca   60
gtta                                                              64

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 47
gactgcgtac caattcaag                                              19

<210> SEQ ID NO 48
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 48
gactgcgtac caattcaca                                              19

<210> SEQ ID NO 49
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 49
gactgcgtac caattcagc                                              19

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 50
gatgagtcct gagtaacac                                              19

```
<210> SEQ ID NO 51
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 51
gatgagtcct gagtaacta                                               19

<210> SEQ ID NO 52
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 52
gatgagtcct gagtaactc                                               19

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 53
gatgagtcct gagtaactg                                               19

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligonucleotide Primer.

<400> SEQUENCE: 54
gatgagtcct gagtaactt                                               19
```

IDENTIFICATION OF POINSETTIA CULTIVARS

RELATED APPLICATIONS

This application claims the benefit of U.S. Provisional Application No. 60/220,854, filed Jul. 26, 2000, and U.S. Provisional Application No. 60/252,206, filed Nov. 21, 2000, the disclosures of which are incorporated herewith by reference in their entireties.

FIELD OF THE INVENTION

This invention relates to methods of identifying plant cultivars using genetic fingerprinting techniques.

BACKGROUND OF THE INVENTION

Ornamental plants such as begonias, geraniums, impatiens, poinsettias and the like comprise a large and profitable market in the United States. For example, sales of poinsettias, one of the best-selling flowering potted plants in the United States, exceeded $220 million dollars in 1998. Many ornamental plants such as poinsettias are vegetatively or clonally propagated (i.e., by cuttings from stock plants). Plants produced in this manner share the same genetic and phenotypic characteristics of the stock plant. Distributors, growers and buyers of ornamental plants are often concerned about the authenticity of the particular variety or cultivar of plant being grown or sold. Accordingly, a need exists for a method to reliably and accurately determine if a particular plant is the same cultivar as another cultivar, or if a particular plant is a member of a particular family or breeding program of plants. Additionally, a need exists for a method of accurately identifying particular cultivars by key characteristics, and then cataloging those characteristics such that plants produced in the future may be compared to the cataloged plants (i.e., in order to determine if a plant is a new cultivar or the same as one already known). Specifically, there is a need for a method that will significantly improve current visual techniques for cataloging that are both time-consuming for the practitioner and prone to producing ambiguous results.

One potential method of confirming the identity of a cultivar is to characterize key genetic traits or patterns of known cultivars, and then compare these traits or patterns with the genetic traits or patterns of the plant whose genetic identity is unknown. Genetic patterns of a particular plant may be obtained by producing a unique "fingerprint" of the genome of the plant, which fingerprint will identify that plant as being of a particular genotype or cultivar.

Over the past 10 years, genetic mapping technologies utilizing analyses of restriction fragment length polymorphisms (RFLP), random amplified polymorphic DNA (RAPD), simple sequence repeats (SSR) and amplified fragment length polymorphisms (AFLP) have been used for identifying genetic markers for desirable traits or phenotypes in plants. These techniques have also been useful adjuncts to genetic and breeding programs for genome mapping and marker-assisted selection, respectively. Using these technologies, attempts have been made to develop cultivar-specific fingerprints for identification.

Unfortunately, the RAPD and RFLP technologies used in previous attempts to fingerprint cultivars lacked the resolution to distinguish between genotypes. While AFLP and SSR techniques generally have sufficient resolution to distinguish between certain genotypes, these methods have heretofore been unable to overcome the problems posed by the inherent heterogeneity in regions of plant genomes that contain polymorphisms, but which are unrelated to the regions of the genomes that are related to cultivar identity. In particular, these technologies have been limited in their use for reliable cultivar identification of vegetatively propagated plants due to recognized and unrecognized regions of heterogeneity in these plant genomes.

Accordingly, the identification of a set of polymorphism-containing restriction fragments strictly associated with cultivar diversity in vegetatively propagated plants remains desirable. Once identified, such a set could be used, for example, to create reference databases containing fingerprints of particular cultivars. The ability to reliably compare fingerprints of individual plant genomes to polymorphic restriction fragments known to be related to cultivar identity would be of value to plant breeders, for example, in monitoring license agreements or authenticating plants that are patented. In plant breeding programs, these methods could be used for monitoring genetic drift and for trait or cultivar selection, while plant growers could use such methods to reliably confirm that they are receiving the cultivars they have purchased. Such methods have heretofore not been available.

SUMMARY OF THE INVENTION

The present inventors have examined over 100 amplified restriction fragments that exhibit polymorphisms between cultivars of the Poinsettia genome, a clonally propagated crop. In particular, the inventor has identified amplified restriction fragments that are polymorphic between genotypes, and which in specific combinations also correlate with cultivar identity. These restriction fragments have the sequences set forth herein as SEQ ID NO:1 through SEQ ID NO:46. The sequences designated herein as SEQ ID NO:1 through SEQ ID NO:46 are sequences of specific domains of the plant genome linked to cultivar differentiation. These sequences may be used to find homologs in other plants, which homologs are also useful in cultivar determination.

A subset of the fragments comprising 16 particular fragments and identified herein as SEQ ID NOS:12, 15-25, 27, 30, 34-37, and 39 may be used to estimate genetic relationships among poinsettia plants and their association with particular breeding programs or families. These polymorphic fragments are correlated with poinsettia cultivar identity. The discovery of regions of the genome that are involved in cultivar differentiation (as distinguished from those which appear as polymorphisms but are in fact not related to cultivar identity) provides an advantageous and significant advancement for the genomic fingerprinting of plants generally, and more specifically of vegetatively propagated plants such as poinsettias.

Accordingly, a first aspect of the invention is a method of assessing the relationship, if any, between a poinsettia plant and a known poinsettia cultivar, by obtaining a DNA fingerprint of the poinsettia plant's genomic DNA by AFLP, the fingerprint being a collection of amplified restriction fragments; comparing the fingerprint so obtained in with a genomic DNA fingerprint of the known poinsettia cultivar; and assessing the relationship between the plant and the cultivar by identifying similarities, if any, between the fingerprints.

A second aspect of the invention is a method of estimating a genetic relationship of a first poinsettia plant to a representative member of a specific breeding family. This method also involves obtaining a DNA fingerprint of the genomic DNA of a first poinsettia plant, where the fingerprint comprises a set of amplified restriction fragments. The fingerprint of the first poinsettia plant is compared with a fingerprint of the genomic DNA of the second poinsettia plant, where the fingerprint comprises a set of amplified restriction fragments. A profile index value is generated based on the comparison of the fingerprint of the first poinsettia plant with the fingerprint of the second plant. Known mathematical models may be used to determine whether the two poinsettia plants belong to a representative breeding family.

A third aspect of the present invention is a method of determining the profile similarity of a first plant to a second plant, by obtaining a DNA fingerprint of the genomic DNA of a first plant by AFLP, wherein the fingerprint comprises a set of amplified restriction fragments and wherein each fragment comprises a DNA sequence that includes a DNA sequence selected from the group consisting of SEQ ID NO:1 to SEQ ID NO:46; comparing the fingerprint of the first plant with a fingerprint of the genomic DNA of the second plant, wherein the fingerprint comprises a set of amplified restriction fragments and wherein each fragment comprises a DNA sequence that includes a DNA sequence selected from the group consisting of SEQ ID NO:1 to SEQ ID NO:46; and generating a profile index value based on the comparison of the fingerprint of the first plant with the fingerprint of the second plant, wherein a profile similarity index value of about 1 or a dissimilarity value of about zero indicates that the two plants are sufficiently genetically similar so as to be of the same cultivar.

A fourth aspect of the present invention is a method of determining the profile similarity of a first poinsettia plant to a second poinsettia plant, by obtaining a DNA fingerprint of the genomic DNA of a first poinsettia plant by AFLP, wherein the fingerprint comprises a set of amplified restriction fragments; comparing the fingerprint of the first poinsettia plant with a fingerprint of the genomic DNA of the second poinsettia plant, wherein the fingerprint comprises a set of amplified restriction fragments; and generating a profile index value based on the comparison of the fingerprint of the first poinsettia plant with the fingerprint of the second plant, wherein a profile similarity index value of about 1 or a dissimilarity value of about zero indicates that the two poinsettia plants are genetically similar.

A fifth aspect of the present invention is a method of generating a profile of a poinsettia plant, wherein the profile comprises the number of amplified restriction fragments having a sequence that includes the sequence selected from the group consisting of SEQ ID NOS:12, 15, 16, 17, 18, 19, 20, 21, 22, 23, 24, 25, 27, 30, 34, 35, 36, 37, 39, 42, and 44, and the identity of each fragment, by obtaining a DNA fingerprint of the genomic DNA of the poinsettia plant, wherein the fingerprint is a set of amplified restriction fragments, and wherein each fragment comprises a DNA sequence that includes a DNA sequence selected from the group consisting of SEQ ID NOS:12, 15, 16, 17, 18, 19, 20, 21, 22, 23, 24, 25, 27, 30, 34, 35, 36, 37, 39, 42, and 44; identifying the amplified restriction fragments having a sequence that includes a sequence selected from the group consisting of SEQ ID NOS: 12, 15, 16, 17, 18, 19, 20, 21, 22, 23, 24, 25, 27, 30, 34, 35, 36, 37, 39, 42, and 44 in the fingerprint; and recording the amplified restriction fragments having a sequence that includes a sequence selected from the group consisting of SEQ ID NOS: 12, 15, 16, 17, 18, 19, 20, 21, 22, 23, 24, 25, 27, 30, 34, 35, 36, 37, 39, 42, and 44, and the identity of each fragment.

A sixth aspect of the present invention is a database comprising the profiles of poinsettia cultivars, wherein the profile of each cultivar comprises the number of restriction fragments possessed by the cultivar and the identity of the restriction fragment, and wherein the restriction fragments are selected from the group of fragments that have a sequence that includes a sequence selected from the group consisting of SEQ ID NOS:12, 15, 16, 17, 18, 19, 20, 21, 22, 23, 24, 25, 27, 30, 34, 35, 36, 37, 39, 42, and 44.

A seventh aspect of the invention is a method of identifying a plant cultivar, by obtaining a first DNA fingerprint of the genomic DNA of the plant, wherein the fingerprint is a set of amplified restriction fragments, and wherein each fragment comprises a DNA sequence that includes a sequence selected from the group consisting of homologs of SEQ ID NO:1 to SEQ ID NO:46; and then comparing the first fingerprint with a second fingerprint comprising a set of amplified restriction fragments of the genomic DNA of a known plant cultivar, wherein each fragment comprises a DNA sequence that includes a sequence selected from the group consisting of homologs of SEQ ID NO:1 to SEQ ID NO:46; wherein the plant cultivar is a representative of the known plant cultivar if the fingerprint of the plant and the fingerprint of the known plant cultivar have the same complement of polymorphic bands.

A eighth aspect of the invention is a method of generating a profile of a plant, wherein the profile comprises the number of amplified restriction fragments having a sequence that includes the sequence selected from the group consisting of SEQ ID NO:1 to SEQ ID NO:46, and the identity of each fragment, by obtaining a DNA fingerprint of the genomic DNA of the plant, wherein the fingerprint is a set of amplified restriction fragments, and wherein each fragment comprises a DNA sequence that includes a DNA sequence selected from the group consisting of SEQ ID NO:1 to SEQ ID NO:46; identifying the amplified restriction fragments having a sequence that includes a sequence selected from the group consisting of SEQ ID NO:1 to SEQ ID NO:46 in the fingerprint; and recording the amplified restriction fragments having a sequence that includes a sequence selected from the group consisting of SEQ ID NO:1 to SEQ ID NO:46, and the identity of each fragment.

A ninth aspect of the invention is a method of determining whether a poinsettia plant is a representative of a known poinsettia cultivar, by obtaining a first DNA fingerprint of the genomic DNA of a poinsettia plant by AFLP analysis, and then comparing the first fingerprint with a second fingerprint of the genomic DNA of the known poinsettia cultivar; wherein the poinsettia plant is a representative of the known poinsettia cultivar if the fingerprint of the poinsettia plant and the fingerprint of the known poinsettia cultivar have the same complement of polymorphic bands.

A tenth aspect of the invention is a method for choosing restriction fragments to be amplified in AFLP analysis of plants comprising the step of identifying sequences that contain homologs of SEQ ID NOS:12, 15, 16, 17, 18, 19, 20, 21, 22, 23, 24, 25, 27, 30, 34, 35, 36, 37, 39, 42, and 44 in plants other than poinsettia.

A eleventh aspect of the invention is a method of choosing primers comprising the step of selecting primers capable of amplifying polymorphisms related to cultivar diversity.

A twelfth aspect of the invention is a method for choosing primers for use in AFLP analysis of poinsettias, by performing AFLP amplification of multiple cultivars using multiple primer pairs; selecting for analysis fragments that are present in at least one cultivar, repeatable in multiple amplifications, and whose bands on the AFLP gel exhibit sufficient intensity and separation from other fragments; eliminating primer pairs that detected intracultivar variation; performing AFLP amplification on multiple genotypes using the remaining primer pairs; and selecting the primer pairs with the highest number of useful polymorphisms.

A thirteenth aspect of the invention is a method of building a database of poinsettia cultivar profiles by generating a profile of a poinsettia cultivar; storing the profile on a computer-readable storage media; and adding addition profiles of poinsettia cultivars to the database as they are generated.

A fourteenth aspect of the invention is a method of utilizing a database of poinsettia cultivar profiles by generating a profile of a poinsettia cultivar; storing the profile on a computer-readable storage media; adding addition profiles of poinsettia cultivars to the database as they are generated; and comparing the profile of the poinsettia cultivar to those profiles in the database to determine the identity of the poinsettia cultivar.

A fifteenth aspect of the invention is a method of distinguishing a poinsettia cultivar from a known poinsettia cultivar, by obtaining a first DNA fingerprint of the genomic DNA of a poinsettia plant by AFLP analysis and then comparing the first fingerprint with a fingerprint of the genomic DNA of the known poinsettia cultivar; wherein the poinsettia plant is not a representative of the known poinsettia cultivar if the fingerprint of the poinsettia plant and the fingerprint of the known poinsettia cultivar are dissimilar.

Additional aspects of the invention include databases that comprise the profiles of poinsettia cultivars, where the profile of each cultivar comprises the number of restriction fragments possessed by the cultivar and the identity of the restriction fragment, and where the restriction fragments are selected from the group of fragments that have a sequence that includes a sequence selected from the group consisting of SEQ ID NO:1 to SEQ ID NO:46. In one embodiment, the database comprises the profiles of poinsettia cultivars, where the profile of each cultivars comprises the number of restriction fragments possessed by the cultivar and the identity of the restriction fragment, and where the restriction fragments are selected from the group of fragments that have a sequence that includes a sequence selected from the group consisting of SEQ ID NOS:12, 15, 16, 17, 18, 19, 20, 21, 22, 23, 24, 25, 27, 30, 34, 35, 36, 37, 39, 42 and 44.

The foregoing and other aspects of the present invention are explained in detail in the specification set forth below.

DETAILED DESCRIPTION OF THE PREFERRED EMBODIMENTS

Figure 1:
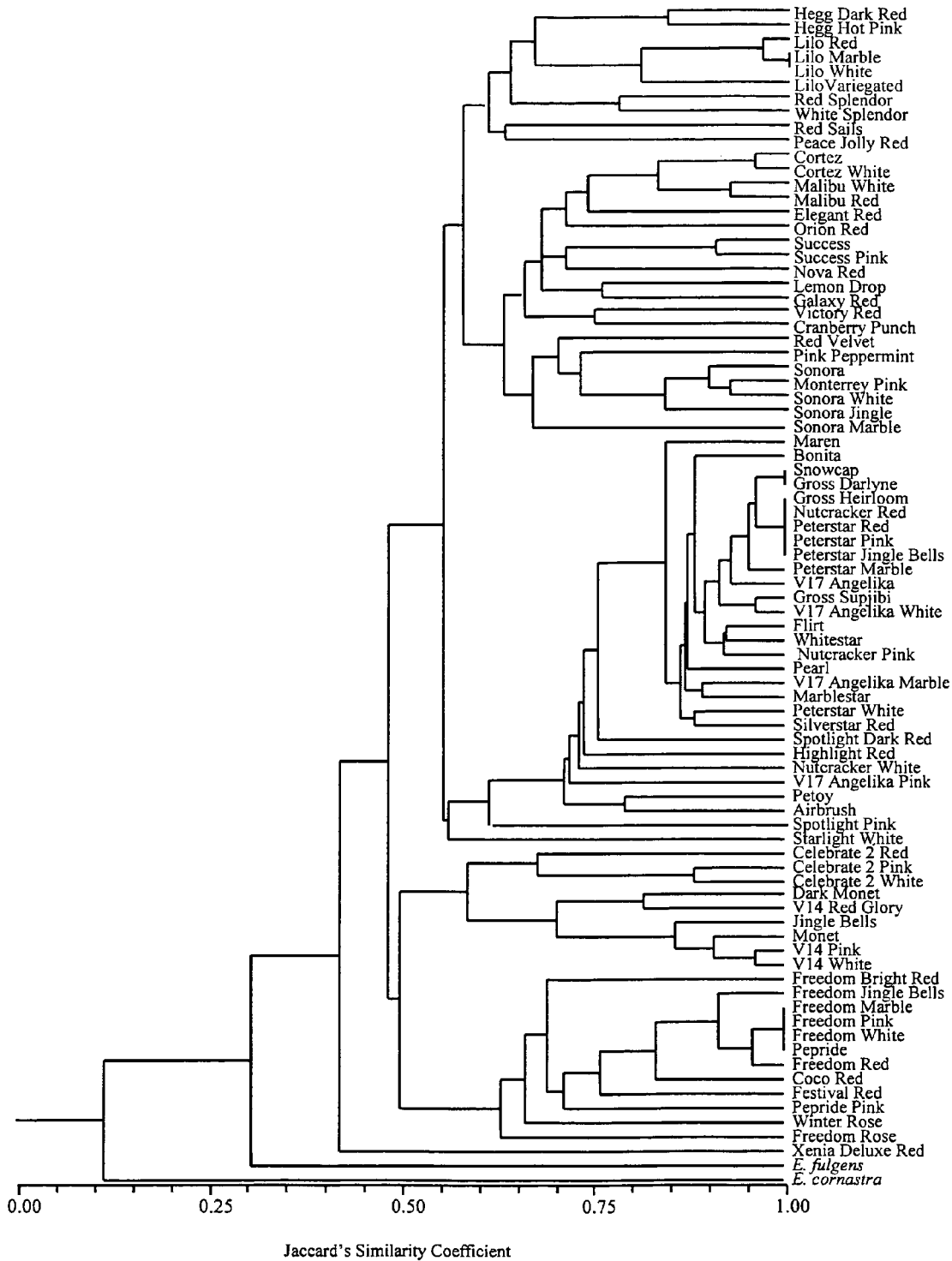
FIG. 1 is a phylogram illustrating the similarities of poinsettia DNA profiles identified by analyzing different combinations of known polymorphisms. This figure compares DNA profiles using 41 polymorphisms (set forth herein as SEQ ID NOS:1-46) selected for profiles that maximize the resolution of related cultivars for identification. This figure further illustrates that in order to resolve genetic differences between cultivars it is desirable to select specific polymorphisms, i.e., that specific polymorphisms are better predictors of parentage than the other polymorphisms for vegetatively propagated crops.

The present invention will now be described more fully hereinafter in the specification, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Nucleotide sequences are presented herein by single strand only, in the 5' to 3' direction, from left to right. Nucleotides are represented herein in the manner recommended by the IUPAC-IUB Biochemical Nomenclature Commission, in accordance with 37 C.F.R. §1.822 and established usage. See, e.g., *Patentin User Manual, pages* 99-102 (November 1990) (U.S. Patent and Trademark Office).

As used herein, the term "cultivar" refers to a man-made plant variety, produced and maintained by vegetative propagation rather than from seed. However, as used herein, the term "cultivar" may also refer to any plant variety with a unique genotype or DNA fingerprint.

The term "polymorphism" refers to a difference in DNA sequence between or among different genomes, cultivars or individuals. Such differences can be detected when they occur within known genomic regions.

The terms "nucleic acid sequence" or "sequence" as used herein, refers to an oligonucleotide, nucleotide, or polynucleotide, and fragments thereof, and to DNA or RNA of genomic or synthetic origin which may be single- or double-stranded, and represent the sense or antisense strand.

Genomic DNA sequences are those naturally occurring DNA sequences constituting the genome of a cell (i.e., a plant cell). Used herein, the term "genomic DNA" generally refers to nucleic acid fragments targeted for amplification and subsequent fingerprinting analysis by any of the fingerprinting techniques described herein. Genomic DNA may be amplified by known procedures as described herein, using suitable primers to produce detectable primer extension products.

The terms "DNA amplification" and "nucleic acid amplification" refer interchangeably herein to any method known in the art that results in the linear or exponential replication of nucleic acid molecules that are copies of a target substrate nucleic acid molecule. Preferably, the target or substrate nucleic acid is DNA. One known method and preferred of DNA amplification is the polymerase chain reaction or "PCR." PCR is based on an enzymatic reaction in which copies of DNA fragments are synthesized from a substrate DNA in vitro. The reaction involves the use of one or more oligonucleotide primers, each of which is complementary to nucleotide sequences flanking a target segment in the substrate DNA. A thermostable DNA polymerase catalyzes the incorporation of nucleotides into the newly synthesized DNA molecules, which serve as templates for continuing rounds of amplification. PCR is generally described in U.S. Pat. Nos. 4,683,195 and 4,683,202 to Mullis et al., the disclosures of which are incorporated by reference in their entirety.

The term "primer" is generally used herein to encompass any synthetic or naturally occurring oligonucleotide that can specifically hydrogen-bond to a region of a nucleic acid (preferably, DNA) molecule, and function to initiate a nucleic acid replication or primer extension process. Such processes may include, for example, PCR, or other enzyme-based amplification reactions. Primers will generally be single-stranded, will be complementary to at least one strand of a target or substrate nucleic acid, and will serve to direct nucleotide polymerization or primer extension using the targeted sequence as a template. Primers of the present invention may be used in combination with another primer to flank the target sequence in PCR, thus forming a "primer set" or "primer pair." In general, primers of the present invention may be as short as 20 nucleotides, or 15 nucleotides, or 10 nucleotides, or even shorter. Primers may be as long as 30 nucleotides, or 40 nucleotides, or 50 nucleotides, or even longer, if desired. In a preferred embodiment of the invention, primers are 15 to 20 nucleotides in length.

The terms "restriction endonuclease" and "restriction enzyme" are used interchangeably herein to refer to enzymes that recognize a specific palindromic-base sequence (target site) in a double-stranded DNA molecule. These enzymes catalyze the cleavage of both strands of the DNA molecule at a particular base in the target site.

The term "restriction fragment" refers to a DNA molecule as produced by digestion with one or more restriction endonucleases. Any given genome may be digested by one or more particular restriction endonucleases into a discrete set of restriction fragments. The DNA restriction fragments that result from restriction endonuclease cleavage may be separated by gel electrophoresis and detected by methods known in the art (e.g., by fluorescence detection, autoradiography, and the like) in order to visualize the location of the restriction fragments on the gel. The DNA restriction fragments will appear on the gel as "bands."

The discrete set of amplified restriction fragments identified as polymorphic, which are produced by the digestion of DNA with one or more restriction endonucleases followed by selective amplification of the resulting fragments, may be referred to as a "fingerprint" of the substrate DNA (e.g., the genomic DNA of a plant). The fingerprint for a cultivar is the subset of polymorphic fragments (the complete set comprising 41 polymorphic fragments) characteristic of that cultivar. In other words, all polymorphic fragments of a cultivar present on a gel, after the DNA of the cultivar has been digested into restriction fragments, amplified, and the fragments separated by, for example, gel electrophoresis, constitute the fingerprint of the cultivar.

The term "ligation" refers to an enzymatic reaction by which two double-stranded DNA molecules are covalently joined together in their sugar-phosphate backbones via phosphodiester bonds. The ligation reaction may be catalyzed by, for example, the enzyme T4 DNA ligase. Ligation can occur between two DNA molecules that each are bounded by blunt (non-staggered) ends (i.e., blunt-end ligation), but also can occur if the two DNA molecules contain single-stranded overhanging ends that are complementary in sequence (e.g., "sticky ends").

The term "adaptor" will refer herein to largely double stranded DNA molecules comprised of a limited number of base pairs, e.g., about three to about thirty base pairs. Adaptors are generally used in the AFLP process further described herein, and are generally comprised of two synthetic single-stranded oligonucleotides having nucleotide sequences in the genome of interest, and which are also, in part, complementary to each other. Under appropriate annealing conditions, the two complementary synthetic oligonucleotides will have single-stranded termini. Generally, single stranded ends of the adaptor molecule ("sticky ends") are designed so that they are complementary to and can be specifically ligated to the digested end of a restriction fragment. However, the ends of the adaptor molecules may be blunt-ended, and may be ligated to the ends of blunt-ended fragments using blunt-end ligation techniques known in the art.

The term "homolog" as used herein, refers to a molecule of the same essential nature. As used herein, it refers to a molecule similar to SEQ ID NO:1 to SEQ ID NO:46 that is related to cultivar diversity.

The methods and sequences of the present invention are particularly useful in identifying plants that are reproduced by vegetative propagation, that is, asexually, in which new plants are formed not from seeds but from specialized structures of the root, stem or leaf (e.g., a "cutting" from a plant). Vegetative propagation, as used herein, is used interchangeably with the term "clonal propagation" and also encompasses the propagation of new plants from meristem cultures. In a preferred embodiment, the present invention is used to identify cultivars of those plants known in the art as "ornamental" plants, which group of plants includes but is not limited to, poinsettias, impatiens, begonias, roses, geraniums, chrysanthemums, and the like, with poinsettias being particularly preferred. Cultivars are defined by like characteristics such as flower color, leaf morphology and color, plant architecture and strength, shelf life, and the like. Accordingly, cultivars in a diversity of species may be defined by homologs of the sequences of the present invention in analogous gene families (i.e., in other ornamental or vegetatively propagated plants).

The methods of the present invention are based on the discovery by the present inventors of a discrete set of polymorphic and selectively amplified restriction fragments that are identified herein as having DNA sequences that include the DNA sequences of SEQ ID NO:1 to SEQ ID NO: 46. As used herein, the terms "fragment" and "polymorphism" may be used interchangeably, whereas the term "sequence" generally refers to the DNA sequence of the fragment. A subset of the fragments comprising 16 particular fragments and including the DNA sequences identified herein as SEQ ID NOS:12, 15-25, 27, 30, 34-37, and 39 may be used to estimate genetic relationships among poinsettia plants and their association with particular breeding programs or families. Poinsettia cultivars from certain breeding programs share certain bands that may be selected from the group of 16 fragments identified above. These polymorphic fragments are correlated with poinsettia cultivar identity. The discrete set of sequences having been identified by using unique combinations of specific primers set forth herein, individual plants may be then analyzed by the techniques described herein for the presence or absence of each of the designated polymorphic fragments that are a measure of diversity in specific regions of the genome.

The presence or absence of the polymorphic fragments may be determined by obtaining a DNA fingerprint of the poinsettia plant, wherein the presence or absence of a particular amplified fragment on a gel correlates with the presence or absence of the sequence corresponding to that polymorphism in the genome of the plant. The presence or absence of a fragment may be determined by determining the location (i.e., the length or size) of "bands" present on a gel in which amplified genomic DNA has been electrophoresed and visualized, as described herein. Similarity of profiles of different plants are based on the number of shared fragments (i.e., the number of fragments that the plants have in common).

A plant that is a member of a particular cultivar will have the same DNA fingerprint (i.e., the same complement of polymorphic bands) as another member of the same cultivar. Because of the variable nature of the sequences, different cultivars will possess different subsets of the 41 fragments. For example, one cultivar may possess 23 of the 41 fragments, while another cultivar may have 30 of the 41 fragments, of which only 20 fragments may be shared. Of course, two different cultivars may have the same number of fragments identified as being fragments of the set of 41, but the specific fragments possessed by each cultivar may differ, thus allowing for differentiation between the cultivars. Two of the 41 fragments (identified herein as fragments 36-161 and 36-162) have more than one sequence assigned to them (i.e., the fragment 36-161 has the three alternative sequences 36-161A, 36-161B, and 36-161C; the fragment 36-162 has the four alternative sequences 36-162A, 36-162B, 36-162C, and 36-162D). Thus, although the number of polymorphic fragments is 41, the total number of sequences that represent the fragments is 46.

For maximum resolution, the presence or absence of each of the 41 fragments may be determined for each plant whose identity is to be confirmed or compared to the identity of another plant or cultivar. However, a subset of the 41 fragments comprising 16 particular fragments and including the DNA sequences identified herein as SEQ ID NOS:12, 15-25, 27, 30, 34-37, and 39) may be used to estimate genetic relationships among poinsettia plants and their association with particular breeding programs or families. The identification of this subset is based on the inventors' discovery that poinsettia cultivars from certain breeding programs share certain bands that may be selected from the group of 16 fragments identified above. Known poinsettia breeding programs that may be identified in this fashion include but are not limited to "families" containing the Freedom, Peterstar and Sonora cultivars.

In one embodiment of the invention, a method of identifying whether or not a particular plant is a member of a known cultivar is carried out as follows: First, genomic DNA from the plant is obtained by one of several methods known in the art. Such methods include but are not limited to the benzyl chloride procedure of Zhu et al., Nucl. Acid Res. 21:5279-5280 (1993), which is a preferred procedure in the practice of the present invention. Other, less preferred DNA extraction methods that may be used include the "CTAB/chloroform" method (see Murray et al., Nucl. Acids Rev. 8:4321-4325 (1980)), or an urea extraction mini-prep procedure such as the method set forth in J. Chen et al., *The Maize Handbook* (in M. Freeling and V. Walbot, eds., Springer-Verlag, New York, pages 526-527 (1994)). The genomic DNA is preferentially obtained from the youngest fully expanded leaf of the plant, according to known techniques.

After the genomic DNA of the plant is obtained, a fingerprint comprising specific restriction fragments of the genomic DNA is generated. The fingerprint may be obtained by any suitable method known in the art, but a preferred method is the AFLP technique, sometimes referred to as the amplified fragment length polymorphism technique. This technique is also referred to herein as "AFLP analysis." This method of selective restriction fragment amplification is set forth in, for example, European Patent 534,858 to M. Zabeau, and P. Vos et al., *Nucl. Acids Res.* 23, 4407-14 (1995), which disclosures are incorporated herein by reference in their entirety. Briefly, the AFLP technique consists of digesting genomic DNA with restriction enzymes, ligating synthetic oligonucleotide adaptors to the ends, using selective PCR primers to amplify a subset of the restriction fragments, and separating the amplified fragments on an appropriate gel system.

In the AFLP technique, restriction fragments are generated from genomic DNA by complete digestion with a restriction enzyme combination. Preferably, AFLP uses a combination of two different restriction enzymes: one enzyme which serves the purpose of targeting rare sequences (a "rare cutter" restriction enzyme), and a second enzyme (a frequent cutter enzyme) which serves the purpose of reducing the size of the restriction fragments to a range of sizes which are amplified efficiently. Targeting rare sequences reduces the complexity of the starting mixture of DNA fragments, thus achieving a more reliable and accurate amplification. Restriction enzymes suitable for the present invention include but are by no means limited to the hexanucleotide recognition site enzymes EcoRl, Dral, Pstl and BamHl; the tetranucleotide recognition site enzymes Sau3Al, Mbol, Msel, Taql, Tsp509l and Alul; the pentanuleotide recognition site enzymes Hinfl or Avall; and the octanucleotide site enzymes, Pmel, Pacl, or Swal. In a preferred embodiment of the present invention, two restriction enzymes are used to digest the DNA, wherein one of the restriction enzymes has a tetranucleotide recognition site, and the other enzyme has a hexanucleotide recognition site.

After digestion of the genomic DNA, double-stranded adaptors comprising oligonucleotides of moderate length (e.g., from about 3 to about 30 base pairs) are specifically ligated to the ends of the restriction fragments. The individual adaptors corresponding to the different restriction sites all carry distinct DNA sequences.

The selective principle upon which the AFLP method is based resides in the design of selective, adaptor-directed amplification (i.e., PCR) primers. In general, these primers are composed of a sequence that matches the adaptor sequence restriction site and additional random nucleotides (e.g., two or three additional nucleotides) at the 3' end. The primers ensure that only those restriction fragments exhibiting a matching sequence will be amplified. Consequently, a subset of the fragments is amplified and can be separated by gel electrophoresis to generate a "fingerprint" of the genomic DNA. Since the 3'-nucleotides must match perfectly in order for the PCR primers to efficiently amplify their target DNA fragment, this selective principle exhibits a high degree of fidelity.

In one embodiment of the invention, the hexanucleotide recognition site restriction enzyme is EcoRl and the tetranucleotide recognition site restriction enzyme Msel. In a preferred embodiment, the primers are selected from the following group of primers:

```
EcoRI primer E2: 5'-GACTGCGTACCAATTCAAG-3'    (SEQ ID
                                               NO:47)

EcoRI primer E3: 5'-GACTGCGTACCAATTCACA-3'    (SEQ ID
                                               NO:48)

EcoRI primer E7: 5'-GACTGCGTACCAATTCAGC-3'    (SEQ ID
                                               NO:49)
```

-continued

```
MseI primer M2:  5'-GATGAGTCCTGAGTAACAC-3'  (SEQ ID
                                            NO:50)

MseI primer M5:  5'-GATGAGTCCTGAGTAACTA-3'  (SEQ ID
                                            NO:51)

MseI primer M6:  5'-GATGAGTCCTGAGTAACTC-3'  (SEQ ID
                                            NO:52)

MseI primer M7:  5'-GATGAGTCCTGAGTAACTG-3'  (SEQ ID
                                            NO:53)

MseI primer M8:  5'-GATGAGTCCTGAGTAACTT-3'  (SEQ ID
                                            NO:54)
```

In a more preferred embodiment of the invention, the following set of primer pairs are used in the AFLP process to elucidate the polymorphic amplified fragments of the present invention:

| | |
|---|---|
| E2 and M5 | E3 and M8 |
| E2 and M7 | E7 and M2 |
| E3 and M5 | E7 and M5 |
| E3 and M6 | E3 and M7 |

An AFLP amplification results in the co-amplification of multiple genomic fragments. Differences in DNA sequence between genomes (e.g., between cultivars) in the region of the restriction sites or the one to ten nucleotides directly adjacent to the restriction sites leads to differences, or polymorphisms, in the PCR products generated.

Each pair of primers used in the AFLP process will generate a certain number of polymorphic fragments that are a subset of the 41 polymorphic fragments and include the DNA sequences set forth herein as SEQ ID NO:1-46. For example, the primer pair of E2 and M5 will yield five polymorphic fragments. Accordingly, in order to obtain the full set of polymorphic fragments which comprise the fingerprint of a cultivar, the amplification of the genomic DNA is preferably performed with all eight primer pairs set forth above; i.e., the amplification procedure is performed with the first primer pair (E2 and M5), then repeated with the second primer pair (E2 and M7), etc., until the entire set of desired fragments is generated. In one embodiment of the invention, one of the primers, preferably the one corresponding to the hexanucleotide-site restriction enzyme, carries a labeling moiety. The labeling moiety may be a fluorophore, chromophore, radioactive isotope (i.e., $P^{33}$), or any other detectable label known to those in the art. In one example of the present invention, the labeling moiety is $P^{33}$.

Other methods of obtaining the fingerprint are arbitrarily primed PCR (AP-PCR) also known as random amplified polymorphic DNA (RAPD), DNA amplification fingerprinting (DAF), arbitrary signatures from amplification profiles (ASAP), simple sequence repeat amplification (SSR), or any other suitable method known in the art.

The AP-PCR (Arbitrarily Primed Polymerase Chain Reaction) method is useful for creating genomic fingerprints from samples for which little is known about the target sequence to be amplified. Performing the first few PCR cycles at low stringency using short arbitrary oligonucleotides (typically 10-20 base pairs) generates strain-specific arrays of DNA fragments (fingerprints). After completion of these early cycles, some of the PCR products will have ends complementary to the primers. The PCR cycles are then completed at higher stringency. DNA amplified in this manner can be used to determine the relatedness of species or for analysis of restriction fragment length polymorphisms (RFLPs). See J. Welsh and M. McClelland, *Nucl. Acids Res.* 18, 7213 (1990). AP-PCR is also called RAPD (Randomly Amplified Polymorphic DNA). J. G. Williams et al., *Nucl. Acids Res.* 18, 6531 (1990).

DAF (DNA Amplification Fingerprinting) involves PCR amplification using a single arbitrary primer. The amplification products are separated on a polyacrylamide gel and detected by silver staining. The electrophoresis pattern can then be used to "fingerprint" the sample. See G. Caetano-Anolles, et al., *Bio/Technology* 9, 553 (1991).

ASAP (Arbitrary Signatures from Amplification Protocols) is a dual-step amplification procedure whereby amplification products generated with arbitrary primers are amplified using mini-hairpin primers containing 3'-terminal, three-nucleotide, arbitrary sequences. T. W. Starman et al., *Hort. Science* 34, 1119 (1999).

SSR uses primers that are complementary to regions flanking microsatellite sequences or "simple-sequence repeats." The genomic segments flanked by the simple-sequence repeats are amplified. Polyacrylamide gels and radioactive labeling may be used to detect polymorphisms.

The amplified fragments produced by the above-described methods or other suitable methods may be separated on a gel by known methods in order to obtain the DNA fingerprint. The separation of amplification nucleic acid fragment products by polyacrylamide or agarose gel electrophoresis, usually followed by staining or visualization, is known. Separation of amplification products can be obtained by other methods, however, which can be used in place of or together with gel electrophoresis. The separation is followed by the determination of the characteristic pattern of fragments by visualizing the characteristic pattern of the nucleic acid on the dried and developed gel. For example, the pattern of DNA fragments may be characterized by Southern blotting to a number of probes, by staining with DNA-binding dyes, by detection of radioactive isotope labels incorporated into the DNA, and other methods that are known in the art. Individual banding pattern differences in the co-amplified fragments between different genomic DNA samples indicate polymorphisms between the source DNA.

The foregoing methods are used to produce a set of amplified DNA fragments unique to each plant and the plants that are of the same cultivar. The discrete set of amplified DNA polymorphic fragments comprises the "fingerprint" of the poinsettia DNA. As set forth above, the term "fingerprint" also refers to the banding pattern (i.e., the location of bands on a gel) of the genomic DNA on the gel, after the DNA has been digested into restriction fragments, amplified, and the fragments separated on the gel.

From the fingerprint, a "profile" of the plant or cultivar may be generated. As used herein, the term "profile" is a description of the polymorphisms detected in the genomic DNA of a particular poinsettia cultivar. In other words, a profile is a description of the subset of the 41 fragments set forth herein that are discovered to be characteristic of that particular cultivar. In general, when a fingerprint is obtained for a particular poinsettia plant by the methods described above, the fingerprint is characterized by detecting the presence or absence of a band corresponding to a particular polymorphic fragment that has a sequence that includes the sequence selected from the group consisting of SEQ ID NO:1: to SEQ ID NO:46. Accordingly, a "profile" of a poinsettia plant's genomic DNA may comprise the specific subset of bands (from the total set of 41 fragments) that the particular plant has. The generation of a profile is generally illustrated by the following example:

the fingerprint of a poinsettia plant is obtained by the methods described therein, and the amplified restriction fragments obtained therefrom separated onto a gel and detected. The plant thus analyzed may have five bands, and the bands may correlate with the restriction fragments known to have the sequences that include the sequences defined herein as SEQ IDS NO:2, 7, 10, 15, 18 and 34. The "profile" of the poinsettia plant or cultivar may thus comprise the number of the bands the plant or cultivar had (i.e., five) and which bands they are (i.e., SEQ IDS NO:2, 7, 10, 15, 18 and 34). Stated another way, a "profile" is a compilation of data about a particular poinsettia plant, which data may include the number of bands that the plant has and the identity of the particular bands.

Fingerprints or profiles of particular plants or cultivars may then be compared to the fingerprints or profiles of other plants or cultivars. This comparison may be carried out by one or more of a diversity of methods according to the present invention. For example, a fingerprint of the DNA of a particular plant may be visually compared to the fingerprint of another plant or cultivar to determine if the banding patterns are identical, similar or dissimilar. In this method, the visualized gel of the separated fragments is visually compared to the gel of the separated fragments of another plant. The gel may be automatically scanned by apparatus (e.g., a phosphor imager) designed to generate an image representative of the gel. The generated image may optionally be stored as a computer file, which may be a set of data, a photographic image, or any other means of storing an image known in the art. The image may also be analyzed by image analysis software known in the art for the presence or absence of bands known to correspond to the 41 polymorphisms of the present invention, the location of the bands, and the number of bands in the fingerprint of the plant.

In a preferred embodiment of the invention, the profile of a particular plant is compared to a database (i.e., a collection of data stored in a computer or in a computer-readable storage media such as a disk or diskette) that comprises the known profiles of numerous poinsettia cultivars. Using software programs and mathematical models known in the art, the profile of a particular plant may be compared to all of the profiles in the database or a subset of the profiles in the database, and a measure of the similarity or dissimilarity between the particular plant and any one or more known profiles generated. The profile comparison may include comparing which bands a particular plant has, versus which bands another cultivar has, and then determining which bands are shared by both plants (wherein the bands represent the particular polymorphic fragments described herein). When two plants have profiles with the same complement of polymorphic bands, then they are considered to be of the same cultivar.

In an embodiment of the invention, the profile generated by the fingerprint of the genomic DNA of a poinsettia is compared to a database comprising the known profiles of other poinsettia plants, and a numeric value (a measure or index of profile similarity or dissimilarity) calculated to represent the similarity of the poinsettia to the poinsettias whose profiles are stored in the database. For example, if two plants are found to have profiles with the same complement of polymorphic bands, the index of profile similarity may have the value of one, while plants that share no bands may have the value of zero. Preferred indices of similarity include the Dice similarity coefficient model (or the "Dice model," L. R. Dice, *Ecology* 26, 297-302 (1945)) and the Jaccard model (P. Jaccard, *Bull. Soc. Vaud. Sci. Nat.* 44, 223-270 (1908)). An index of dissimilarity may also be used, wherein zero indicates identity between profiles. A preferred index of dissimilarity is the Lynch model (M. Lynch, *Mol. Biol. Evol.* 5, 584-599 (1988)).

Under these various analysis system, plants of varying profile similarity will accordingly have values between zero and one.

Figure 2:
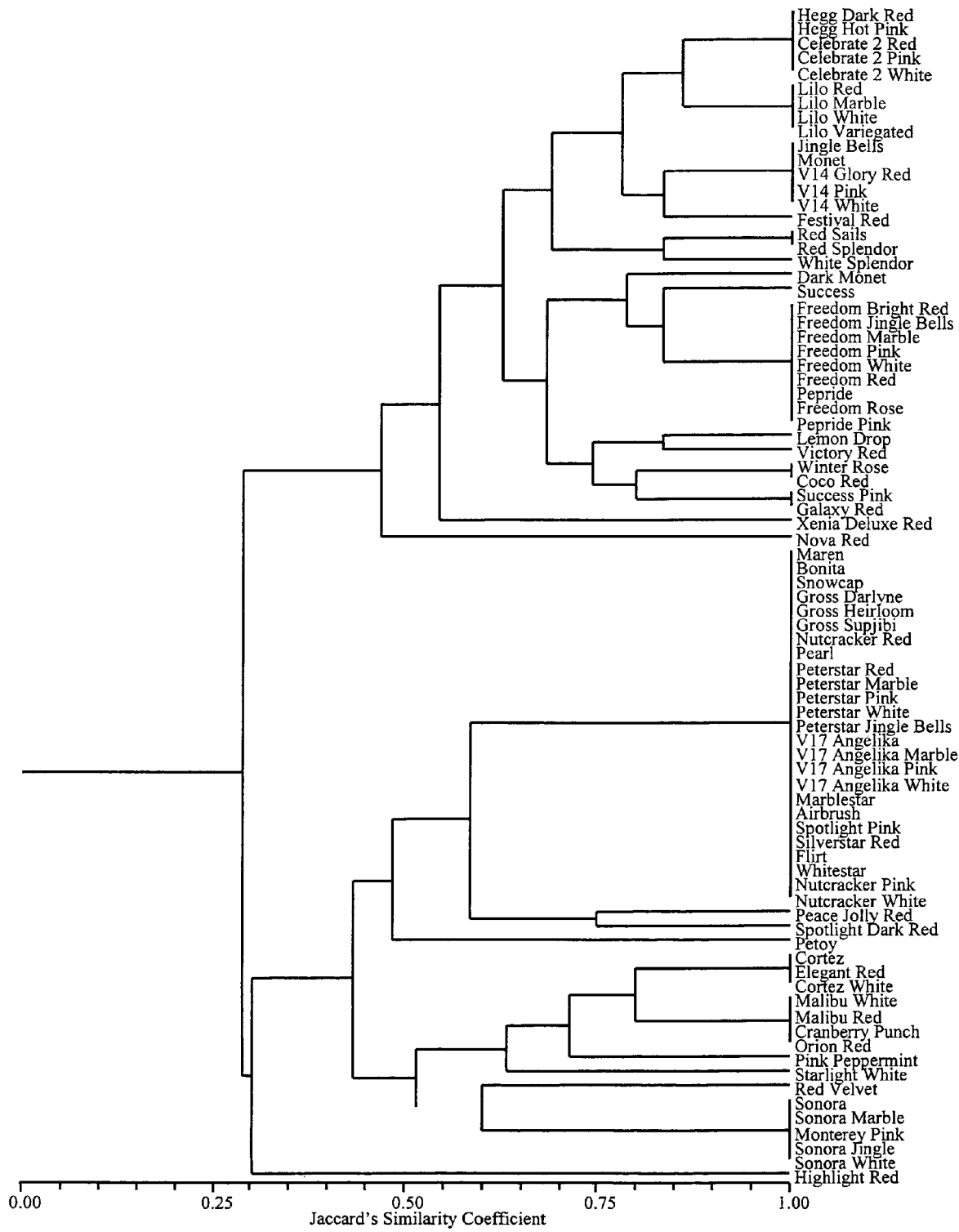
FIG. 2 is a phylogram comparing poinsettia DNA profiles obtained by fingerprinting genomic DNA of certain poinsettia plants, and then analyzing a set of seven of the sixteen fragments selected for their collective ability to group cultivars by genetic background. The polymorphisms used are those set forth herein as having DNA sequences including the DNA sequences of SEQ ID NOS:12, 20, 21, 22, 23, 24, 34, 35 and 37.
Figure 3:
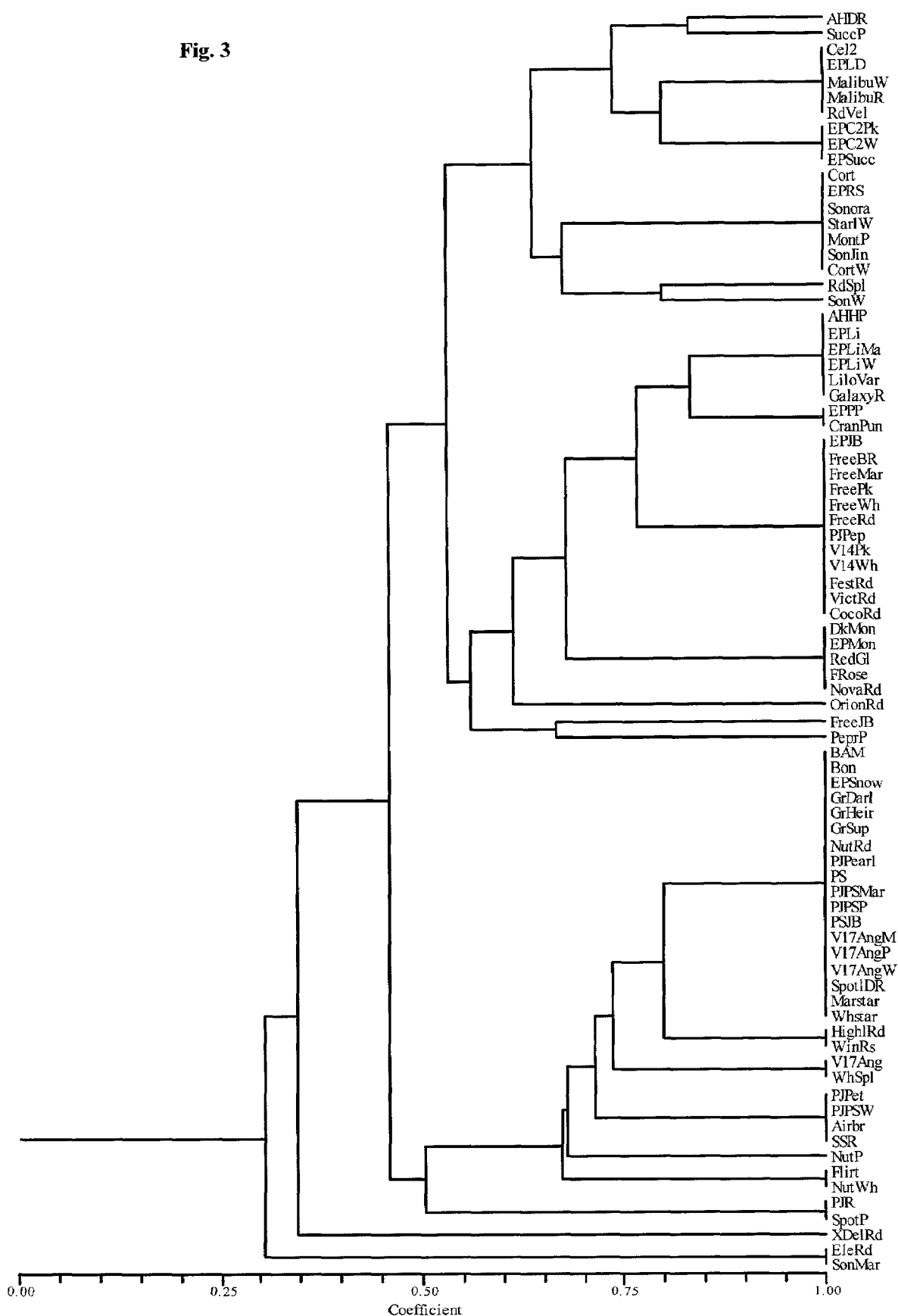
FIG. 3 is a phylogram comparing poinsettia DNA profiles obtained by fingerprinting genomic DNA of certain poinsettia plants, and then analyzing a set of seven randomly selected polymorphisms. The data provided in this Figure demonstrate the significance of the discovery of the selective polymorphisms of the present invention.

In one embodiment of the invention, the Dice model is used in conjunction with the statistical software package known as NUMERICAL TAXONOMY AND MULTIVARIATE ANALYSIS SYSTEM VERSION 2.0 or NTSYSpc Version 2.0, available from Exeter Software, Setauket, N.Y. See also, F. James Rohlf, *NTSYSpc Users Guide* (Applied Biostatistics Inc., Setauket, N.Y. (1998). The software package is used to generate indices of profile similarity between plants. Using this system of analysis, the profile of each plant comprises data indicating the presence or absence of each of the 41 polymorphic fragments (or alternatively a subset of the 41 fragments), wherein a value of zero is assigned if a particular band is absent and value of one assigned if a band is present. Profile similarities are estimated from the 1/0 data using an equation in which the variables include the number of positive matches between two cultivars, and the number of fragments in each of the individual cultivars. This calculation includes only positive matches (1/1, i.e., each cultivar shares the same band), and excludes negative matches (0/0, i.e., both cultivars lack the band). A value of one indicates the plants have the same complement of polymorphic bands, while a value of zero indicates that the plants share no bands. Generally, similarity measurements of about one indicate a high degree of similarity and may be differentiated by phenotype. Phylograms such as those in FIGS. 1 to 3 may thus be generated from these similarity indices, and the similarities between many cultivars analyzed.

Embodiments of the invention in include the databases themselves, as described and used above. These databases preferably comprise the profiles of poinsettia cultivars, where the profile of each cultivar comprises the number of restriction fragments possessed by the cultivar and the identity of the restriction fragment, and where the restriction fragments are selected from the group of fragments that have a sequence that includes a sequence selected from the group consisting of SEQ ID NO:1 to SEQ ID NO:46. In one preferred embodiment, the database comprises the profiles of poinsettia cultivars, where the profile of each cultivars comprises the number of restriction fragments possessed by the cultivar and the identity of the restriction fragment, and where the restriction fragments are selected from the group of fragments that have a sequence that includes a sequence selected from the group consisting of SEQ ID NOS:12, 15, 16, 17, 18, 19, 20, 21, 22, 23, 24, 25, 27, 30, 34, 35, 36, 37, 39, 42 and 44.

Databases, and database systems, methods and computer program products generally include a database that actually stores the data, a database management system and one or more applications that interface with the database management system to provide, for example, user interfaces and other applications.

The present invention may take the form of a computer program product on a computer-usable storage medium having computer-usable program code and/or the database itself embodied in the medium. A computer-usable or computer-readable medium may be any medium that can contain, store, communicate, propagate, or transport the database and/or associated programs for use by or in connection with a program execution system, apparatus, or device. Any suitable computer readable medium may be utilized including hard disks, CD-ROMs, optical storage devices, a transmission media such as those supporting the Internet or an intranet and/or magnetic storage devices.

The database and/or the programs that perform calculations and comparisons as described herein may exist and/or execute entirely on a user's computer, partly on a user's computer, as a stand-alone software package, partly on the user's computer and partly on a remote computer, or entirely on the remote computer. The present invention may thus be embodied in hardware and/or in software (including firmware, resident software, micro-code, etc.). Furthermore, the present invention (e.g., a database or program that utilizes the database) may take the form of a computer program product on a computer-usable or computer-readable storage medium having computer-usable or computer-readable program code embodied in the medium for use by or in connection with an instruction execution system.

The following Examples are provided to illustrate the present invention, and are not to be construed as limiting thereof.

EXAMPLE 1

Isolation and Amplification of Poinsettia Restriction Fragments

Genomic DNA was isolated from fully expanded poinsettia leaves using a modified benzyl chloride procedure (see Zhu et al, *NucL. Acid Res.* 21, 5279-5280 (1993)) and quantified by spectrophotometry. The AFLP protocol was performed essentially as described by Vos et al., *Nucleic Acids Research* 23, 4407-4414 (1995), using the commercially available AFLP Analysis System I™ (Life Technologies, Gaithersburg, Md.). The modifications made to the Life Technologies protocol included extending the length of time for the restriction digest incubation to an overnight incubation and extending the length of time for the ligation incubation to six hours at a lower temperature than that suggested by the manufacturer, in order to improve reproducibility in the final AFLP result. The AFLP fragments were electrophoresed on a 6% denaturing acrylamide gel for approximately two hours. The gel was fixed and dried, then exposed to a phosphor screen overnight. The screen was then scanned on a phosphorimager (Molecular Dynamics, Sunnyvale, Calif.), and the image was saved as a Tagged Image File Format (TIFF) file. Analysis of the image was facilitated by the use of image analysis software (Pro-RFLP™ from DNA ProScan, Nashville, Tenn.), with which specific polymorphic fragments were scored for presence or absence.

EXAMPLE 2

Optimization of AFLP Analysis by Obtaining Optimal Primer Pairs

To determine optimal primer pairs for AFLP of poinsettia genomes, a two-level screening strategy was employed. Initially, four phytoplasma-free cultivars were tested with 64 primer pairs using AFLP Analysis System I™.

This screening allowed for a determination as to which primers were appropriate to use with poinsettia, and provided a first estimate of the number of polymorphisms each primer pair would detect that would allow us to differentiate different cultivars. The best four of these primer pairs were chosen based on the overall quality of the AFLP amplification and the number of fragment differences between the different cultivars. These four primer pairs were used to begin the AFLP evaluation of 70 cultivars. Fragments were selected for analysis if they were present in at least one phytoplasma-free cultivar, repeatable in multiple amplifications, and easily scored on the AFLP gel in terms of intensity and separation from other fragments. Sixty-six fragments were located that fit these requirements, and provided enough polymorphism to distinguish most of the 70 collected cultivars collected. These fragments were then tested for intracultivar variation using 77 samples from nine different cultivars collected from locations worldwide. It was determined that 44 of the fragments varied greatly in at least one cultivar, and most varied in several. Eliminating these hypervariable fragments from analysis left 22 validated fragments, and necessitated an additional primer screening to discover which other primer pairs would provide additional reliable polymorphisms.

EXAMPLE 3

Secondary Primer Screening

The secondary primer screening began by selecting the 30 best primer pairs from the first screening using the same criteria as previously described. Twelve poinsettia genotypes were then chosen to screen the 30 primer pairs. Three genotypes served as controls for intracultivar variation and the remaining nine were chosen for their low distance classes. The primer pairs with the highest number of useful polymorphisms were scored and analyzed individually, then in different combinations until the distance classes were optimized.

The 32 fragments generated by the four most useful primer pairs were tested for intracultivar variation, and 19 of them were validated. These 19 fragments were added to the final database, bringing the total number of scored fragments to 41.

EXAMPLE 4

Polymorphic Fragment Sequencing

Sequence data of the polymorphic fragments that were found to correlate with cultivar identity was obtained by isolating each of the scored fragments from an acrylamide gel and first sequencing it using the EcoRl primer. The sequence data was then confirmed by sequencing a second time using the Msel primer. Two of the fragments (36-161 and 36-162) had more than one sequence assigned to them (i.e., 36-161A, 36-161B, 36-161C, 36-162A, 36-162B, 36-162C, and 36-162D), thus bringing the total number of sequences to 46.

The sequences of the 41 polymorphic fragments (the 46 sequences) that correlate with cultivar identity are set forth below. In the following sequences, primer sequences are not shown, and the nucleotide 'N' represents a position in the sequence in which the nucleotide was not determined. Additionally, all sequences are oriented with the EcoRl primer end first and the Msel primer end last.

25-409 (SEQ ID NO:1)
AAACTTAGACTTTATACCATAATNTTTTAGTTGCTGCTTGATCTATAGCA

GTTGAGCCACATAACTTCTGGCAGCCATGTACTCAGCTTCAGCTGTACTT

AGAGCCATAGAAGTTTATTTCTTGTTGTACCATGTGTCTAGACAATTACC

AAGGAAATGACATCCTCTAGTGGTGTTTTTCCTTTCTAACTTGTNTCTTC

CATAATTAGCATTTGTGTATGCCCTCAGAGTGAAATTTCCATTTCTTGGA

TACCATAAACCTGCATCAATAGTTCCTAGCAAATACCATAACAACAGCTA

AGTGAGATTCTCTGGGGTTAGCTTGATATCTACCATAATAACATACAACA

TATTGAATTTCAGGCCTACTAG

25-237 (SEQ ID NO:2)
GTTAGAAAAGCAAATTTCAGTGCAGGGTGTGGATNTGGTGCCAGNTANTA
TTGCAAATGTTAGAGCTTTGTTGCAGGATTTGACTGAGAGGAATTGTGTC
ATGGAGAGAAGTTCGAGTGCGAGCCCGATTGTGTTGTAGGAGAAGAAATT
GGANAGAAGNCGTTGGGGGCAAGTATGGAGTTGAGAATCCCAC
ATCTA

25-222 (SEQ ID NO:3)
AGTTAGAAAAGCAAATTTCAGTGCAGGGTATACTATTGCAAATGTTAGAG
CTTTGTTGCAGGATTTGACAGAGAGGAATTGTATCATGGAGAGAAGTTCG
AGTGCGAGCCCGATTGTGTTGTAGGAGAAGAAATTGGAAGAAGACGTTGG
GGGCAAGTGTGGAGTTGAGAATCCCACATGTA

25-197 (SEQ ID NO:4)
TGCTTCCAAGGTGTTTCTCCTTTTGATAGAGAAATTTTACCAACTATGGA
AAACTGACATGATTTCAGCCTCTCTTCATAAAGATTTTGAGGAATCTGAA
TTGCTTTGTATCTCCCACTTGCGTCAATGATTTGTGAGTTCAGGGTTGGA
GCAGATATCTA

25-139 (SEQ ID NO:5)
CGACGATGGCAATGATGACAATTCTTGCCTGGAACCAGAAATGATAATTG
ATACTCCCTATATAGGGAGAATGTTGAAAATTAGATTTTGAAGTTGTTAT
TTA

27-410 (SEQ ID NO:6)
TTCCATGGTACCTTTGTTCAGTAAAAAAATTACACAATTAGCTAGTTCGA
AGAATACACGTGCAAACTAATTTTTAGGTCNTGGTTGCAAATTATTTTGC
AAAAATAATTACCAAGCTATCTCTTCCAAGTATATATTTCTCTAGCATCT
CCCATGCATAAGAACTGTTGGAGTGTATATGTATGAGAAAGAAATGTATA
ATACCAACCTCTTCCATTTGCTTTGTTCTACTGCTTTCCAAGTGCTCGGT
TTAGGTGTATTACAAGGCCCTATAGTAGCCTGCAGTCATTCATGGAACTA
ACAAACTCAGTATCTAAGCCCGGGGTGAAAAGATACTCACAATCTCACAT
TTCCGATCAACTCCCCATATC

27-286 (SEQ ID NO:7)
GAAAATATGTGCTGAATTTATNCTGTAAAGTAGTTTCGATGCAACCACTG
TTTAGCTTATACTTAACTTTCTGTTCATCACCATCAATCCTCAGCAAAAC
ACCCTCATTCTTCATACTTAGATGTTGTTCGAAGAAATATGGGGTAACAG
NGATTTCTTTGCCCTGGACCTTGGNTTGAAGAGCATCAAACTTGGCGTGA
ACACTAAGAATCTCATAGAACTCCCTTGACTAAGTCAGGATATGTGG

27-257 (SEQ ID NO:8)
AGCTCTTCATTGCTTCATCATAGGTTATCGGTTTATCATCCTCTATGATA
TATAGTTCCCTACATCAGTGATGATGCAACCATATCTTTTAGGACCGTTA
TGAATATGACCTGATCTTTGCATTGATTGTGTTTCAACAGGTTGTTCATT
GGATCAAACCTTCTTGTGTATCTAGAATGGGGTCAACTAGTTGATTATCT
GTTTTATATTCTTGAAGCTCC

27-213 (SEQ ID NO:9)
TGCATTCCATGGTTCAAAAGCCGAGTTTCTTCGCCTCATCGAGTTTTTAT
TCGCAAAGTGGATGGTTTAGACAGGGTTTTGACCAGCAGCCTGGAGTTGG
GAGATTGTTGGCCTCATCAGAAATTAGTTTTCATGGAGTTGGGAGATTTG
AAGGTAATTCAAGGAAGTTTTCTGCA

27-113 (SEQ ID NO:10)
CCGGATAAAAGCACTACAATCAGGTAGATGACTCGGGTCGGATACGTAGT
GCANTACTGAGTCAGACTAACGA

27-112 (SEQ ID NO:11)
GTTTATCTTCAAGTCTAACAAGACCCAGTTTTTCAGATTCCTTTCCTCAA
TTTCTCGTTCAGTTATAAAAGCTAA

27-103 (SEQ ID NO:12)
GAATGCCTATTACATCGGAAAACAAAAAAACAAAGATAAATGCTAGAGAC
ANTATAATCATCCC

27-97 (SEQ ID NO:13)
GTCTTTCTAGTTTTACTGATTTCTGTTGTACTTCTATTAGATATATATTG
TATATCTGA

27-88 (SEQ ID NO:14)
TTGAAGGCAGGAAAATATATCCTATTCTGAAAGGATTTACAATCTGCGG

36-257 (SEQ ID NO:15)
ACTTCTCTCCCCACACAATGTGTAGTGCAGCTAGTGCCGATGACAGTGAG
AAGACCAGAATCACATAGAGAGCGATCGTATGAAAAGGTATTGAATTAGG
GATTTGATGAAAGGGTAAGATAGAAAGGGAGTTGGTGTTAGCGAGTTGTT
TCTCCTGCCCTCACAATAATACTTTTATCAATTTTTCAGTAACAATTTGT
CCATGTACTTTTGGAC

36-161A (SEQ ID NO:16)
TGTGCTCTTGTTCCTTGGATCAAATAAGGAAACATGGCCTTAGGTAAGTG
TAGTCATATCTTTTTGGCTCATGAACCCTAAGTCCCCTATAGTTTGAACA
AGGTTGTGTAGGATTGGTAT

36-161B (SEQ ID NO:17)
AGAACCTAATCTAAGTAGAATCTTATAAAAGAAATGAAAACTTTGAGAGA
TATTTTTAGTATGAAAATAGAAAATAAATCATAAAGTAAACAAGCACAAA
TACCAGCTGGATTTTTCTAA

36-161C (SEQ ID NO:18)
GAATGTGCTCTTGGTCCTTGGGATCTAAATAAGGAAACATGGCCTTGGTA
TAGTAATAATACTTTTTGCTCATAACCCTGAGTCCGCTATGGCTGAACAA
GGTTGTGCAGGATGGTAT

36-161D (SEQ ID NO:19)
AGAACCTAAATCTAGGTAGCCTTCTTATAAAAGAAAATGAAAACTTTGAG
AGATATTTTTAGTATGAAAATAGAAAATAAAATCATAAGTAACAGCACAA
TTACCAGCTGGACTCTC

36-162A (SEQ ID NO:20)
GAATGTGCTCTTGGTTCCTTAGGGATCTAAATAAGGAAACATGGCTTGGT
ATAGTAATAATACTTTTGGCTCATGAACTCTAGTCCTATGCTACAGGTGT
CAGATGATA

36-162B (SEQ ID NO:21)
GATGTGCTCTTGGTCCTGGATCTAATGAAACATGCCTTGTATTAGTAAAA
ATACCTTTTTGGCTATGAACCCTGAGTCCCCTATGGCTTGAAAAAGGTTG
TGCAGGATTGGTAT

36-162C (SEQ ID NO:22)
TTTCTCTCTGATTACATTACTATGTAAAGACCTAAATGAATGAGTTTTCT
TCGCAAGGACCAAATCGAGATATTTTAACTAATTTTTTCTCTTGAAATAT
TTTATCTAGATGAAATTTT

36-155 (SEQ ID NO:23)
GCTTTCTTACATTCTTGGGGACAAGAATGCTTTGAAGGGGAGGGTATTGT
CAGGAGGAAGTAATATAATCTGATTGTTATTTAGTTTATTTGCTTTGGGT
AAATAAGTTGACTATG

38-379 (SEQ ID NO:24)
CTCCAAGGCTTCATTGATGCAGATTATGGTAGAGATACTCTTGAGAGAAA
GAGTACATCAGAGGTTGTCACTTCTAGGGAGATTGCTTAGTATCTTGGTA
CAGCAAGAAGCAAACTTCAGTTGCTTTATCTACTATAGAAGTAGAATATA
TGGCAGCTAGAAGTTGTGTAGCTCAACTTCTTTGGATCAAGCAACAACTA
GAAGATTATGGAGTCTAATCCGGGTGTGTGGATGTAATGTGTGATTACAA
AAGTGCCATTGATGTGTCAAACAATCCAGTATTCCATAGGAGGATAAAAC
ATGTCAACATAAGGCATCGTGAAGAGAAGAAANTTG

38-274 (SEQ ID NO:25)
CAGGANATGAACTTTGATTTCACCANCATAGATTTTGAATCTCAGTCTTC
AGGAAGCTTTTTCAGTTCTTGAGCACATGTTCTGAAAAAATATCAAATCT
CTACATTGTTTTCAAGGTCAACAAATGACCGGTAAGGCTCGGGTTGGTCT
AGACCGGGCACATCAATTTGGGGACAAATTTGAATCCATTTTATCCTACT
TTTTTGTATTGGCAGTAAGGATTAGGATTCTC

38-198 (SEQ ID NO:26)
CTCTCCTATATTTTAGGGTTTAGCTTTGTATCATAAGCTCTTCTGCTCTC
TACCCCTCTAAACCACCCCATGNTATATATGGTATTCATCACTCGAATAT
TTATGTAAGTCATCCATCTCATTCAGGGTTTGATTCGGGCTGATCATCTT
CCGGTTTCTCTAGCTAA

38-139 (SEQ ID NO:27)
TTTGCAGGAGTACTGTCCATGTAAATTTGAGACTTCGCACTATCATTGCA
AGCAATAGCAATAGAAGAAACATCATTTTGCAGCTTACTAATACACCCAC
TC

35-418 (SEQ ID NO:28)
GCCTAGAAAGGTTTTCTAGTCAACATACTCACGTAGCTCACTTTTACCCT
AACTTTTGCCTAGAACGTCCTTTTTGAATTTTCAGTCTAGCGGGCTATTT
TGCACCCTAACTTTTGCCTGAATGGTTTGTAGAATACCAAATAGCGGGAT
ATGCCCTAATTTTGCCTAAGCAGTAGAGGACCACTCATCGGGTGATTTAT
TTTGATTATTTTTTGTGTGCCGCTTTTCTGGATTTGATTCTTTTAGATTA
GATATGATAATGCTTCAATCGATCCTGATTGATAGGGTTTGTGAATTGGT
ACGCAGCC

35-181 (SEQ ID NO:29)
AAGACCAAGTCAGGAGCATACCTAAGAAGAAGGAATAGCTGACCTAGCCG
ATCCTCTGGTACCTCAACTATGGATGGACCCCCGTGTACCTCTCAGTCCT
CCTCCTCGTCATCATATCATCATCCTCGTTGTTGCTC

35-179 (SEQ ID NO:30)
TTATCATAATCAATGTCAATAAAAAAAAAAAGGCAATAAATAAAAGATAA
ATAATTCTGATAGACTAAAAAGAGCAAGGCTGATGCAAAAGTCAGAATAA
GTCTGCTGGATTGAAATCGAAAGGTATCTAGGCAA

35-177 (SEQ ID NO:31)
GGCCCTTTCTCAGCCATGATATCTAAATATACGAGTCTTGTGTGTACGCC
ATTGCATCTCTAGCCCTTCTCCAGGGGGCGTTCTCATCTTGTCCATGCCA
TAATACAATTTCATATATTCTCTCTCCNAGTAAGCAACC

37-329 (SEQ ID NO:32)
AACCTCATCAATCAGGATCAGATGAAGCATTATCATATCTAATCGAAAAG
AATCAAATCTAGAAAAGCGGCACATAAAAGTATATAAAAAAATCACCCGA
CGAGTAGTCTTCTACTGCTCAGGCAAAAATTAGGGTGTATCCTGTTGTTT
GGTAATCTGTAAACCATTCAGGAAAATGTTAGGGTGCAAGAATAACCCGC
TAGACTGAAAATCTGAAAAGGATGGTCTAGGCAAAATTTAGGGTAAAAGT
GAGCTACAATAGTGTGTTGGCTTGAAAACTT

37-248 (SEQ ID NO:33)
GGATTACTGATAATGTTGACAATGGCTTGAGGGCAGTATCTTGCAACTCC
CTCGCAAAGGGTTTTCACTATTCCGGCATTTATGTTGAATAAATCGTCCC
TAGTCATTCCTGGCTTCCTAGGAACCCCAGCAGGAATTATCACAAGATCC
ATTCCTGTAAGAGCATCGTCTAGTTGCTGCTGGCCCAAGAAACCACGCAC
CTGAAAATCAT

72-358 (SEQ ID NO:34)
TTAGCTCGATCTCCATGATCACAAAACTAGTTATCACACCCACCATTTAC
ATTGTTGTTATGCAACAAAGTCAACTGTACTAGAGATTCTCGTCCCGAAG
TGCCCTCAAGATGGGATCGTTTTCTTNATCTATGTNGTAGTNGTCGTNGT
CGTCATCATCCAGGTCATCCAGTATTGATTGGTTGATCCTTNTGCGAGAC
TTTCTTCTATGCNTTCTTGGGCTCCAAACGAGGTTCAGCTTGCTGTACTC
CCATATCACCCACTTTGAACCTGCAGAGTAGCATAACGAACAAGAAAATG
AATGATAGTAGAATAAATTT

72-312 (SEQ ID NO:35)
TATGGTATTTCTTTTCTGGGTGTAATTGATTTGCAACTTGAGTCAAACAG
GTTCTATCAACTGATTTTTCTAGTTTTCGGCGCTTACTGCAACCCTGGAA
AGGATGTTCACTGTTTTTTCCTTCGTTTTCCAGGTCAGCAATACGACGAG
TAATTTCCTCGGTATCATATATGGATTCCAGCTTGTAATCTTTTATGCAT
TGAAATACGGCTTTACGAGCAGCTAGTTCTCTCTCCCTGGCCTTCTCCTG
CAGATGAAATCAGGAGTTATAT

72-235 (SEQ ID NO:36)
CAGATTATTTGACTATAATTAGTTTGGCTTCTATGGTTGCTGCACTAAAT
GATCATCGAAACAGCCAATCGGTTCATGGGTTTGTCATGAGAAAAGGCTG
GTTCATGGAATATATTGTCATTGGGAATGCAACTGTGGACATGTATGCTA
AAATTGGAGCCACAGATACGGCCCGTGCAGTATTTGAAAGCCTAC

72-210 (SEQ ID NO:37)
TTTCAAAAGTTGAAAAGAATATGTCATAAGCCTTACACTAGTAAATGGAA
CTATAGTCCGTGCCCCCTACATCAAAAGATCAATGATAAAGAAGAACAAA

```
ACACTCCAAAGAGCAATTCTTCTCAAAAGGTGCTGAGCTGGAATCCCATT

CTAATCGTGGCATCCCTCCCC 72-162 (SEQ ID NO:38)
AAATGTAGCAAAGAACATTATCAACAAATGCCCCAAAAAACAAGTGAAAA

TATAATCACCACTGAAGCAAAAAAAGTAAGTAAAAACAGAAGAAAAGACA

ACTAAATGTAGATTATTACA 72-127 (SEQ ID NO:39)
AACTTTTTTCTTTGTATAATTATCTCATATTTTTTGTGAATATTCTTGTT

TGAATAGAACACACTTTATATATGAAACCCACTTTATC 72-105 (SEQ ID NO:40)
ATCCTTTTCAACAAGGACATCGATGAAAAGTGATTTATAAATGTGGATAT

GTAAATCTAGCTTAGTG 75-263 (SEQ ID NO:41)
CCAGGAGTAAAATAGCCATTATGAAAGTACCATTGAACCATATTGCTAAC

ATCCTTGCCGACCAGGTCCCAAAAGTGTTGATAAAAAATACCAGTAAAGC

CGTCAGGACCCAGCGCACTATCACCCTTCATCGAGAAGACTCTATTTCGA

ATTTCATCAAAAGAAGGCTTCCTAATGAACTCATCATTGTCGCTGCCCGT

CACCCGATTAGGAACTGTCTGCC 75-201 (SEQ ID NO:42)
CTAACTGGATGCAAGAAATGAGCAGGCACCGATGAACTAGCAAATAAAGG

TGGCAGCATCAGAACCACCATCGTAACCACCGTTAGAATCGCCGCCCGAT

GAAAGCCCCTGCATTCTTTTCAAATACAATCTATACTTCTTGCATCATGA

ACCCTACGTTTTCTC 75-145 (SEQ ID NO:43)
ACTAATCCCATATTAGATGGGAATTGGATCGCTTGACATGAGAGATTTCA

AATGAACTTTATTTCCATCCCTAGAGCCGAGTTCATAAAATCTCTCCTAA

ACCCAT 75-106 (SEQ ID NO:44)
TGCACCATTTGCATTTTCACACAACCATTTATAATAATATTCATCCCATA

NGTTTGAGGGTTTTCGG 75-104 (SEQ ID NO:45)
GTTCGTATATGTAATATATCCTNGTAAAGTTTAATTACAGAAACATNGCA 75-102 (SEQ ID NO:46)
CGTACCAGCGGAGACGATGGCCTGAAATTTGAGCACCTTCCGTTGCATCA

GAGTTTCTCAGTTA
```

In addition to determining the 41 fragments and 46 sequences, the present inventor found that sixteen fragments (comprising 21 sequences) were particularly useful in estimating whether two cultivars were from the same breeding program, since cultivars of the same breeding programs tended to share bands selected from the set of sixteen fragments, identified as follows:

| | |
|---|---|
| 27-103 | (SEQ ID NO: 12) |
| 36-257 | (SEQ ID NO: 15) |
| 36-161 | (SEQ ID NOS: 16, 17, 18, 19) |
| 36-162 | (SEQ ID NOS: 20, 21, 22) |
| 36-155 | (SEQ ID NO: 23) |
| 38-379 | (SEQ ID NO: 24) |
| 38-274 | (SEQ ID NO: 25) |
| 38-139 | (SEQ ID NO: 27) |
| 35-179 | (SEQ ID NO: 30) |
| 72-358 | (SEQ ID NO: 34) |
| 72-312 | (SEQ ID NO: 35) |
| 72-235 | (SEQ ID NO: 36) |
| 72-210 | (SEQ ID NO: 37) |
| 72-127 | (SEQ ID NO: 39) |
| 75-201 | (SEQ ID NO: 42) |
| 75-106 | (SEQ ID NO: 44) |

EXAMPLE 5

Statistical Analysis of Poinsettia Amplified Fragments

Scored data of poinsettia plants were exported as one (when a band representing one of the 41 polymorphisms is present) or zero (when a band representing one of the 41 polymorphisms is absent) to a Microsoft Excel™ spreadsheet. Several models for calculation of distance matrices that incorporate only positive matches (1/1) were evaluated, including the similarity models by Dice and Jaccard in the statistical software package NTSYSpc (supra). The similarity model chosen for this Example was the Dice model, as described above. A dendrogram (a graphic display of the similarities of the individual cultivar indices) is generated using the unweighted pair group method with arithmetic mean (UPGMA) or "NEIGHBOR" distance matrix program of the software package known as the Phylogeny Inference Package (PHYLIP) (Version 3.5c, 1993, available from Joseph Felsenstein, The University of Washington, Seattle, Wash.).

The foregoing is illustrative of the present invention and is not to be construed as limiting thereof. The invention is defined by the following claims, with equivalents of the claims to be included therein.

That which is claimed is:

1. A method of estimating a genetic relationship between a poinsettia plant and a known poinsettia cultivar, the method comprising the steps of:
   (a) obtaining a DNA fingerprint of the poinsettia plant's genomic DNA by AFLP, the fingerprint comprising a collection of amplified polymorphic restriction fragments;
   (b) comparing the fingerprint obtained in (a) with a genomic DNA fingerprint of the known poinsettia cultivar; and
   (c) estimating the genetic relationship between the plant and the cultivar by determining the degree of similarity between the fingerprints,
   wherein the amplified polymorphic restriction fragments comprise DNA sequences that include DNA sequences SEQ ID NOS: 12, 20, 21, 22, 23, 24, 34, 35, and 37.

2. A method of assessing the breeding history of a first poinsettia plant, comprising:
   (a) obtaining a DNA fingerprint of the genomic DNA of a first poinsettia plant by AFLP, wherein the fingerprint comprises a set of amplified polymorphic restriction fragments;
   (b) comparing the fingerprint of the first poinsettia plant with a fingerprint of the genomic DNA of a poinsettia plant that is a representative member of a specific breeding family, wherein the fingerprint comprises a set of amplified polymorphic restriction fragments; and
   (c) generating a profile index value based on the comparison of the fingerprint of the first poinsettia plant with the fingerprint of the poinsettia plant that is a representative member of a specific breeding family, thereby assessing the breeding history of a poinsettia plant,
   wherein the amplified polymorphic restriction fragments comprise DNA sequences that include DNA sequences SEQ ID NOS: 12, 20, 21, 22, 23, 24, 34, 35, and 37.

3. The method of claim 2, wherein the specific breeding family is selected from the group consisting of the Freedom, Peterstar, and Sonora breeding family.

4. The method according to claim 2, wherein the AFLP analysis is carried out by first digesting the genomic DNA with a restriction enzyme that has a tetranucleotide recognition site and a restriction enzyme that has a hexanucleotide recognition site.

5. The method according to claim 4, wherein the restriction enzyme that has a tetranucleotide recognition site is MseI, and the restriction enzyme that has a hexanucleotide recognition site is EcoRI.

6. A method of assessing the breeding history of a first poinsettia plant, comprising:

(a) obtaining a DNA fingerprint of the genomic DNA of a first poinsettia plant by AFLP, wherein the fingerprint comprises a set of amplified polymorphic restriction fragments;

(b) comparing the fingerprint of the first poinsettia plant with a fingerprint of the genomic DNA of a poinsettia plant that is a representative member of a specific breeding family, wherein the fingerprint comprises a set of amplified polymorphic restriction fragments; and (c) generating a profile index value based on the comparison of the fingerprint of the first poinsettia plant with the fingerprint of the poinsettia plant that is a representative member of a specific breeding family, thereby assessing the breeding history of a poinsettia plant, wherein the fingerprint of the genomic DNA of the first poinsettia plant is used to generate a profile of the poinsettia plant, wherein the profile comprises the set of amplified polymorphic restriction fragments that comprise DNA sequences that include the DNA sequences SEQ ID NOS: 12, 20, 21, 22, 23, 24, 34, 35, and 37; and wherein (b) comprises comparing the profile of the poinsettia plant to a profile generated from the fingerprint of the poinsettia plant that is a representative member of a specific breeding family, wherein the profile of the poinsettia plant that is a representative member of a specific breeding family comprises the set of amplified polymorphic restriction fragments that comprise DNA sequences that include the DNA sequences SEQ ID NOS: 12, 20, 21, 22, 23, 24, 34, 35 and 37.

7. The method of claim 6, wherein the profile of at least one of the first poinsettia plant and the profile of the poinsettia plant that is a representative member of a specific breeding family is stored in a database comprising profiles of known poinsettia cultivars, and wherein the profiles of the known poinsettia cultivars comprise the set of amplified polymorphic restriction fragments that comprise DNA sequences that include the DNA sequences SEQ ID NOS: 12, 20, 21, 22, 23, 24, 34, 35, and 37.

8. A method of determining the profile similarity of a first poinsettia plant to a second poinsettia plant, comprising:

(a) obtaining a DNA fingerprint of the genomic DNA of a first poinsettia plant by AFLP, wherein the fingerprint comprises a set of amplified polymorphic restriction fragments;

(b) comparing the fingerprint of the first poinsettia plant with a fingerprint of the genomic DNA of the second poinsettia plant, wherein the fingerprint comprises a set of amplified polymorphic restriction fragments and (c) generating a profile index value based on the comparison of the fingerprint of the first poinsettia plant with the fingerprint of the second poinsettia plant, thereby estimating the profile similarity of the first poinsettia plant to the second poinsettia plant, wherein the amplified polymorphic restriction fragments comprise DNA sequences that include DNA sequences SEQ ID NOS: 12, 20, 21, 22, 23, 24, 34, 35, and 37.

9. The method according to claim 8, wherein the AFLP analysis is carried out by first digesting the genomic DNA with a restriction enzyme that has a tetranucleotide recognition site and a restriction enzyme that has a hexanucleotide recognition site.

10. The method according to claim 9, wherein the restriction enzyme that has a tetranucleotide recognition site is MseI, and the restriction enzyme that has a hexanucleotide recognition site is EcoRI.

11. A method of determining the profile similarity of a first poinsettia plant to a second poinsettia plant, comprising:

(a) obtaining a DNA fingerprint of the genomic DNA of a first poinsettia plant by AFLP, wherein the fingerprint comprises a set of amplified polymorphic restriction fragments;

(b) comparing the fingerprint of the first poinsettia plant with a fingerprint of the genomic DNA of the second poinsettia plant, wherein the fingerprint comprises a set of amplified polymorphic restriction fragments; and (c) generating a profile index value based on the comparison of the fingerprint of the first poinsettia plant with the fingerprint of the second poinsettia plant, thereby estimating the profile similarity of the first poinsettia plant to the second poinsettia plant, wherein the fingerprint of the genomic DNA of the first poinsettia plant is used to generate a profile of the poinsettia plant, wherein the profile comprises the set of amplified polymorphic restriction fragments that comprise DNA sequences that include the DNA sequences SEQ ID NOS: 12, 20, 21, 22, 23, 24, 34, 35, and 37; and wherein (b) comprises comparing the profile of the poinsettia plant to a profile generated from the fingerprint of the second poinsettia plant, wherein the profile of the second poinsettia plant comprises the set of amplified polymorphic restriction fragments that comprise DNA sequences that include the DNA sequences SEQ ID NOS: 12, 20, 21, 22, 23, 24, 34, 35, and 37.

12. The method of claim 11, wherein the profile of at least one of the first and the second poinsettia plants is stored in a database comprising profiles of known poinsettia cultivars, and wherein the profiles of the known poinsettia cultivars comprise the set of amplified polymorphic restriction fragments that comprise the DNA sequences SEQ ID NOS: 12, 20, 21, 22, 23, 24, 34, 35, and 37.

13. The method according to claim 12, wherein the database is stored in a computer-readable storage medium.

14. The method according to claim 8, wherein the comparing step is carried out by a computer.

15. A method of determining whether a poinsettia plant is a representative of a known poinsettia cultivar, comprising:

(a) obtaining a DNA fingerprint of the genomic DNA of a poinsettia plant by AFLP analysis; and (b) comparing the fingerprint of (a) with a fingerprint of the genomic DNA of the known poinsettia cultivar;

wherein the poinsettia plant is a representative of the known poinsettia cultivar if the fingerprint of the poinsettia plant and the fingerprint of the known poinsettia cultivar have the same complement of polymorphic bands, wherein the DNA fingerprint of the genomic DNA is a set of amplified polymorphic restriction fragments, and wherein the amplified polymorphic restriction fragments comprise DNA sequences that include DNA sequences SEQ ID NOS: 12, 20, 21, 22, 23, 24, 34, 35, and 37.

16. The method of claim 15, wherein the comparison between the profile of the poinsettia plant and the known poinsettia cultivar is carried out by a computer.

* * * * *

UNITED STATES PATENT AND TRADEMARK OFFICE
CERTIFICATE OF CORRECTION

| | | |
|---|---|---|
| PATENT NO. | : 7,695,901 B2 | Page 1 of 1 |
| APPLICATION NO. | : 09/912072 | |
| DATED | : April 13, 2010 | |
| INVENTOR(S) | : Moyer et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (87) days Delete the phrase "by 87 days" and insert -- by 302 days --

Signed and Sealed this

Twenty-fifth Day of May, 2010

David J. Kappos
*Director of the United States Patent and Trademark Office*